(12) United States Patent
Matsubara et al.

(10) Patent No.: US 6,696,573 B1
(45) Date of Patent: Feb. 24, 2004

(54) PROCESSES FOR THE PREPARATION OF TRICYCLIC AMINO ALCOHOL DERIVATIVES

(75) Inventors: Koki Matsubara, Fuji (JP); Naoyuki Ishii, Nobeoka (JP); Masami Ogawa, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 9 days.

(21) Appl. No.: 10/070,249

(22) PCT Filed: Aug. 18, 2000

(86) PCT No.: PCT/JP00/05561
§ 371 (c)(1),
(2), (4) Date: Mar. 4, 2002

(87) PCT Pub. No.: WO01/17962
PCT Pub. Date: Mar. 15, 2001

(30) Foreign Application Priority Data

Sep. 3, 1999 (JP) ............................................. 11-250848
Feb. 8, 2000 (JP) ........................................ 2000-030826

(51) Int. Cl.[7] .................... C07D 209/88; C07D 307/91; C07D 333/76
(52) U.S. Cl. .......................... 548/444; 549/58; 549/460
(58) Field of Search ........................... 548/444; 549/48, 549/460

(56) References Cited

FOREIGN PATENT DOCUMENTS

| EP | 30030 | 6/1981 |
|---|---|---|
| EP | 431943 | 6/1991 |
| EP | 73516 | 10/1996 |
| FR | 2515177 | 4/1983 |
| WO | WO 97/25311 | 7/1997 |
| WO | WO 99/01431 | 1/1999 |
| WO | WO 00/35890 | 6/2000 |
| WO | WO 00/58287 | 10/2000 |

OTHER PUBLICATIONS

S.J. Pasaribu et al., Synthesis of Phenethanolamine Derivatives with Potential β–adrenergic antagonistic activity, Aust. J. Chem., (1975), pp. 1023–1030.

Chemicla Abstracts, vol. 54, Column 13041, Par. b–f, (RN= 13425–36–0) (1959).

*Primary Examiner*—Joseph K. McKane
*Assistant Examiner*—Sonya Wright
(74) *Attorney, Agent, or Firm*—Young & Thompson

(57) ABSTRACT

A process for the preparation of tricyclic amino alcohol derivatives including 2-[N-[2-(9H-carbazol-2-yloxy)ethyl]]amino-1-[(3-methylsulfonylamino)phenyl]ethanol useful in the treatment of diabetes, obesity, hyperlipidemia and so on; and intermediates as represented by formula (5) or (6) or the like useful in the preparation, wherein R11 is hydrogen or the like; and *1 represents an asymmetric carbon atom. 2-Halo-1-(3-nitrophenyl)ethanone derivatives and 1-(3-nitrophenyl)oxirane derivatives, which are intermediates for the preparation of tricyclic amino alcohol derivatives, are easy of purification, and particularly optically active 1-(3-nitrophenyl)oxirane derivatives are effective in enhancing the optical purities of the final products.

3 Claims, No Drawings

PROCESSES FOR THE PREPARATION OF TRICYCLIC AMINO ALCOHOL DERIVATIVES

This application is a 371 of PCT/JP00/05561 filed Aug. 18, 2000.

FIELD OF THE INVENTION

The present invention relates to a novel process for the preparation of tricyclic amino alcohol derivatives of the formula (1):

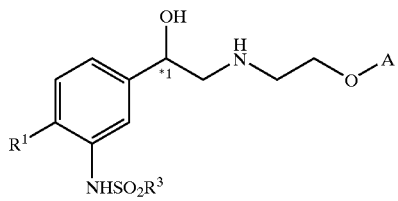

wherein
$R^1$ represents a hydrogen or halogen atom, or a hydroxyl group,
$R^3$ represents a lower alkyl group or a benzyl group,
*1 represents an asymmetric carbon atom, and
A represents one of the following groups:

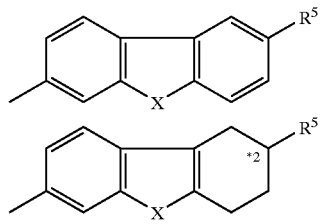

wherein X represents NH, O or S, $R^5$ represents a hydrogen atom or a hydroxyl, amino or acetylamino group, and *2 represents an asymmetric carbon atom when $R^5$ is not a hydrogen atom, or salts thereof, which are useful in the treatment and prevention of diabetes, obesity, hyperlipidemia and the like; and intermediates useful for the process.

BACKGROUND OF THE INVENTION

JP-A-9-249623 (WO97/25311) and WO99/01431 disclose in detail processes for the preparation of compounds of the abovementioned formula (1) and also describe that these compounds are very useful for treating and preventing diabetes, obesity, hyperlipidemia and the like.

However, the study on the above known processes carried out by the present inventors has shown that these processes are not necessarily practical. There would be a need for a more convenient, practical preparation process with low cost which comprises a small number of steps with good industrial efficiency.

DISCLOSURE OF THE INVENTION

Chapter 1

The study carried out by the present inventors showed some disadvantages involved in the conventional processes for the preparation of a compound of the formula (1) set forth above, wherein the disadvantages were that the processes require many reaction steps and several purifying operation including column chromatography, and did not necessarily provide a good yield. In addition, if an optical isomer, such as R-form, of a compound of the formula (1) is to be finally obtained according to the synthesizing route disclosed in the above patent publications, the carbonyl group should be reduced with a borane as a reducing agent in the presence of a chiral auxiliary agent of the following formula (15):

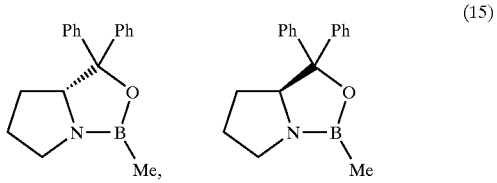

This chiral auxiliary agent is very expensive and the process for the preparation thereof is very complicated. The chiral auxiliary agent is a hazardous, combustible substance and an asymmetric reduction using the said chiral auxiliary agent requires strictly anhydrous conditions, strict temperature controls, complicated works and the like, which will become problematic when the chiral auxiliary agent is industrially used.

In order to solve the above problems, the present inventors have examined a variety of synthesizing processes. As a result, the present inventors have established preferred synthesizing processes successfully and completed the present invention.

That is, the present invention is a process for the preparation of a compound of the formula (1):

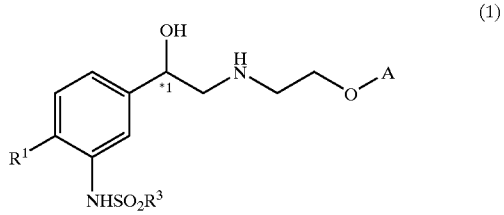

wherein $R^1$ represents a hydrogen or halogen atom, or a hydroxyl group, $R^3$ represents a lower alkyl group or a benzyl group, *1 represents an asymmetric carbon atom, and A represents one of the following groups:

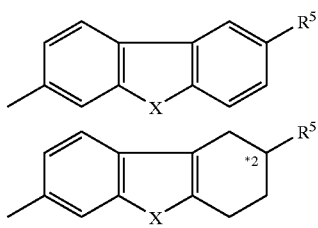

wherein X represents NH, O or S, $R^5$ represents a hydrogen atom, or a hydroxyl, amino or acetylamino group, *2 represents an asymmetric carbon atom when $R^5$ is not a hydrogen atom, said process comprising:

reducing a compound of the formula (7):

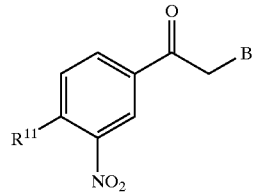

wherein $R^{11}$ represents a hydrogen or halogen atom, or a protected hydroxyl group, B represents a chlorine or bromine atom, to give a halohydrin of the formula (6):

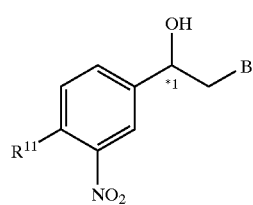

wherein $R^{11}$, B and *1 are as defined above; and, converting the halohydrin under alkaline conditions into an epoxy compound of the formula (5):

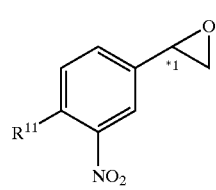

wherein $R^{11}$ and *1 are as defined above; and, reacting the epoxy compound with a compound of the formula (9):

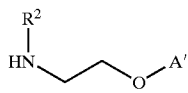

wherein $R^2$ represents an amino-protecting group, and A' represents one of the following groups:

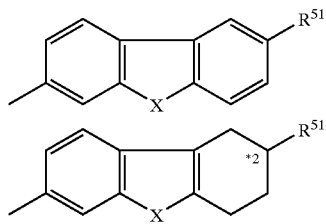

wherein X represents NH, O or S, $R^{51}$ represents a hydrogen atom, a protected hydroxyl group, a protected amino group or an acetylamino group, and *2 represents an asymmetric carbon atom when $R^{51}$ is not a hydrogen atom, to give an amino alcohol of the formula (4):

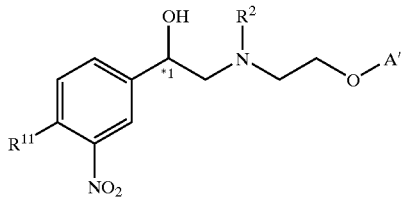

wherein $R^{11}$, $R^2$, A' and *1 are as defined above; and, reducing the nitro group to give an aniline derivative of the formula (3):

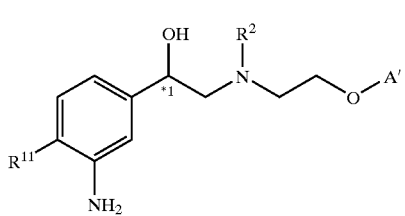

wherein $R^{11}$, $R^2$, A' and *1 are as defined above; and, reacting the aniline derivative with a sulfonating agent to give an amino alcohol of the formula (2):

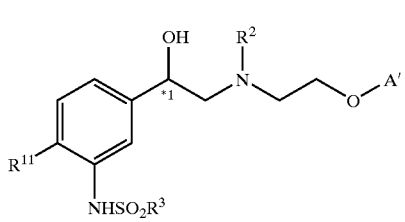

wherein $R^3$, $R^{11}$, $R^2$, A' and *1 are as defined above; and then, simultaneously or sequentially removing the protecting groups to give the compound of the formula (1).

In the aspect of the synthesizing route set forth above, compounds of the formulae (7) and (5) are preferred intermediates which are good in crystallinity. These compounds do not need a column chromatography purifying step and may be used in the following reaction step after being subjected to a recrystallizing treatment and the like. Particularly, the compound of the formula (5), which can be improved in its optical purity by recrystallizing treatment, is useful intermediate.

Specific examples of the compound of the formula (7) include:

2-chloro-1-(3-nitrophenyl)ethanone,
2-chloro-1-(4-benzyloxy-3-nitrophenyl)ethanone,
2-chloro-1-(4-chloro-3-nitrophenyl)ethanone,
2-chloro-1-(4-bromo-3-nitrophenyl)ethanone,
2-bromo-1-(3-nitrophenyl)ethanone,
2-bromo-1-(4-benzyloxy-3-nitrophenyl)ethanone,
2-bromo-1-(4-chloro-3-nitrophenyl)ethanone,
2-bromo-1-(4-bromo-3-nitrophenyl)ethanone and the like.

Specific examples of the compound of the formula (5) include:

(±)-1-(3-nitrophenyl)oxirane,
(±)-1-(4-benzyloxy-3-nitrophenyl)oxirane,
(±)-1-(4-chloro-3-nitrophenyl)oxirane,
(±)-1-(4-bromo-3-nitrophenyl)oxirane and the like. Particularly preferred examples include:
(R)-1-(3-nitrophenyl)oxirane,
(R)-1-(4-benzyloxy-3-nitrophenyl)oxirane,
(R)-1-(4-chloro-3-nitrophenyl)oxirane,
(R)-1-(4-bromo-3-nitrophenyl)oxirane and the like.

In the steps above, the step of reducing the compound of the formula (7) to give a compound of the formula (6) is especially characteristic.

Specific examples of the compound of the formula (6) include:

(±)-2-chloro-1-(3-nitrophenyl)ethanol,
(±)-2-chloro-1-(4-benzyloxy-3-nitrophenyl)ethanol,
(±)-2-chloro-1-(4-chloro-3-nitrophenyl)ethanol,
(±)-2-chloro-1-(4-bromo-3-nitrophenyl)ethanol,
(±)-2-bromo-1-(3-nitrophenyl)ethanol,
(±)-2-bromo-1-(4-benzyloxy-3-nitrophenyl)ethanol,
(±)-2-bromo-1-(4-chloro-3-nitrophenyl)ethanol,
(±)-2-bromo-1-(4-bromo-3-nitrophenyl)ethanol and the like.
Particularly preferred examples include:
(R)-2-chloro-1-(3-nitrophenyl)ethanol,
(R)-2-chloro-1-(4-benzyloxy-3-nitrophenyl)ethanol,
(R)-2-chloro-1-(4-chloro-3-nitrophenyl)ethanol,
(R)-2-chloro-1-(4-bromo-3-nitrophenyl)ethanol,
(R)-2-bromo-1-(3-nitrophenyl)ethanol,
(R)-2-bromo-1-(4-benzyloxy-3-nitrophenyl)ethanol,
(R)-2-bromo-1-(4-chloro-3-nitrophenyl)ethanol,
(R)-2-bromo-1-(4-bromo-3-nitrophenyl)ethanol and the like.

In addition, when one of optical isomers of a compound of the formula (1) is to be obtained in the steps set forth above, a compound of the formula (7) is preferably subjected to an asymmetrical reduction. In this case, the resulting halohydrin compound of the formula (6), and the resulting compounds of the formulae (5), (4), (3), (2) and (1) are obtained as one of their optical isomers, respectively. This step is characteristic of these steps.

In the synthesizing route set forth above, compounds of the formulae (4) and (3) are also preferred intermediates which are novel. This compound does not necessarily need a column chromatography purifying step and may be used in the following reaction step after being subjected to a recrystallizing treatment and the like.

Specific examples of the compounds of the formula (4) include:

(±)-2-[N-benzyl-N-[2-(9H-carbazol-2-yloxy)ethyl]]amino-1-(3-nitrophenyl)ethanol,
(±)-2-[N-benzyl-N-[2-(9H-carbazol-2-yloxy)ethyl]]amino-1-(4-benzyloxy-3-nitrophenyl)ethanol,
(±)-2-[N-benzyl-N-[2-(9H-carbazol-2-yloxy)ethyl]]amino-1-(4-chloro-3-nitrophenyl)ethanol,
(±)-2-[N-benzyl-N-[2-(9H-carbazol-2-yloxy)ethyl]]amino-1-(4-bromo-3-nitrophenyl)ethanol, and salts thereof.
Additional preferred examples include:
(R)-2-[N-benzyl-N-[2-(9H-carbazol-2-yloxy)ethyl]]amino-1-(3-nitrophenyl)ethanol,
(R)-2-[N-benzyl-N-[2-(9H-carbazol-2-yloxy)ethyl]]amino-1-(4-benzyloxy-3-nitrophenyl)ethanol,
(R)-2-[N-benzyl-N-[2-(9H-carbazol-2-yloxy)ethyl]]amino-1-(4-chloro-3-nitrophenyl)ethanol,
(R)-2-[N-benzyl-N-[2-(9H-carbazol-2-yloxy) ethyl]]amino-1-(4-bromo-3-nitrophenyl)ethanol, and salts thereof.

Specific examples of the compounds of the formula (3) include:

(±)-2-[N-benzyl-N-[2-(9H-carbazol-2-yloxy)ethyl]]amino-1-(3-aminophenyl)ethanol,
(±)-2-[N-benzyl-N-[2-(9H-carbazol-2-yloxy)ethyl]]amino-1-(3-amino-4-benzyloxyphenyl)ethanol,
(±)-2-[N-benzyl-N-[2-(9H-carbazol-2-yloxy)ethyl]]amino-1-(3-amino-4-chlorophenyl)ethanol,
(±)-2-[N-benzyl-N-[2-(9H-carbazol-2-yloxy)ethyl]]amino-1-(3-amino-4-bromophenyl)ethanol, and salts thereof.
Additional preferred examples include:
(R)-2-[N-benzyl-N-[2-(9H-carbazol-2-yloxy)ethyl]]amino-1-(3-aminophenyl)ethanol,
(R)-2-[N-benzyl-N-[2-(9H-carbazol-2-yloxy)ethyl]]amino-1-(3-amino-4-benzyloxyphenyl)ethanol,
(R)-2-[N-benzyl-N-[2-(9H-carbazol-2-yloxy)ethyl]]amino-1-(3-amino-4-chlorophenyl)ethanol,
(R)-2-[N-benzyl-N-[2-(9H-carbazol-2-yloxy)ethyl]]amino-1-(3-amino-4-bromophenyl)ethanol, and salts thereof.

In the coupling reaction of the compound of the formula (5) and the compound of the formula (9) in the synthesizing route set forth above, $R^{11}$ in the formula (5) is more preferably a hydrogen or halogen atom.

This specification includes all of the contents as disclosed in the specification and/or drawings of Japanese Patent Applications Nos. 11-250848 and 2000-30826, which are the basis of the priority right of the present application.

PREFERRED EMBODIMENT OF THE INVENTION

In the present invention, $R^{11}$ and $R^1$ may be a hydrogen atom, a halogen atom, or a hydroxyl group (or a protected hydroxyl group for $R^{11}$) with a hydrogen or halogen atom being particularly preferred. The halogen atom may include fluorine, chlorine, bromine and iodine atoms with chlorine and bromine atoms being particularly preferred.

The term "lower" used herein for the lower alkyl group means a linear or branched saturated hydrocarbon containing 1 to 6 carbon atoms and preferred examples thereof include linear or branched alkyl groups, such as methyl, ethyl, n-propyl, i-propyl, n-butyl, i-butyl, s-butyl, t-butyl, pentyl, hexyl and the like, and cycloalkyl groups, such as for example cyclopropyl, cyclobutyl, cyclopentyl, cyclohexyl and the like, with methyl being particularly preferred.

$R^3$ may preferably be the above mentioned lower alkyl group with methyl group being particularly preferred. Benzyl group may be also preferred.

$R^2$ is a protecting group for the amino group and the protecting group for amino groups may be exemplified by, for example, an acyl group or an easily removable aralkyl group. The easily removable aralkyl group may be, for example, an aralkyl group containing 7 to 16 carbon atoms. Specific examples thereof may include, for example, benzyl, phenethyl, 3-phenylpropyl, and 4-phenylbutyl groups, and (1-naphthyl)methyl, 2-(1-naphthyl)ethyl, 2-(2-naphthyl) ethyl groups. They may be optionally substituted at any appropriate site(s) on the phenyl or naphthyl group with any appropriate substituent(s), such as alkyl and alkoxy groups or halogen atom(s). Particularly preferred may be a benzyl group.

It is particularly preferred that B is a chlorine atom.

It is particularly preferred that A is a carbazole group.

A preferred example of $R^5$ may be a hydrogen atom. Alternatively, $R^5$ may preferably be a hydroxyl group. A preferred example of $R^{51}$ may be a hydrogen atom. Alternatively, $R^{51}$ may preferably be a hydroxyl group protected with a protecting group.

In each compound of the above formulae (1), (2), (3), (4), (5) and (6), *1 represents an asymmetric carbon atom, so that there exist two optical isomers. Thus, the present invention encompasses within its scope not only optically pure isomers of these compounds but also any mixtures of two isomers. For example, a preferred configuration of the asymmetric carbon may be exemplified by the absolute configuration R from the viewpoint of pharmacological activities exhibited.

*2 represents an asymmetric carbon atom and there exist two optical isomers. Thus, not only optically pure isomers of these compounds but also any mixtures of two isomers are encompassed within the scope of the present invention.

The protecting group for the protected hydroxyl group represented by $R^{11}$ is not particularly limited, but any conventional one may be used. For example, conventionally easily and selectively removable protecting groups which are preferred may include an aralkyl group, a trialkylsilyl group, an alkoxyalkyl group, an acyl group and the like. These hydroxyl-protecting groups may be introduced and deprotected by known methods described in literatures (for example, T. W. Greene, P. G. M. Wuts, et al., *Protective Groups in Organic Synthesis*, Wiley-Interscience Publication). For example, benzyl groups may be introduced by the action of a benzylating agent, such as benzyl chloride, benzyl bromide, benzyl iodide, or benzyl sulfonate, on phenol in the presence of an acid scavenger. Generally, the amount of benzylating agent added may be about 1 to 5 times by mole based on phenol. In general, this reaction may preferably be carried out in a solvent medium. The medium may include acetone, tetrahydrofuran, 1,4-dioxane, acetonitrile, benzene, toluene, dichloromethane, chloroform, water, methanol, ethanol and the like. The medium may be preferably N,N-dimethylformamide. The amount of medium used may be about 1 to 5 ml per g of phenol. The acid scavenger may include sodium hydroxide, potassium hydroxide, sodium carbonate, cesium carbonate, sodium hydride, sodium and the like. The acid scavenger may be preferably potassium carbonate. Generally, the amount of acid scavenger added may be about 1 to 5 times by mole based on the alcohol. In general, this reaction may be preferably carried out at about –20 to 150° C., particularly about 0 to 100° C., for about 1 to 5 hours.

The hydroxyl-protecting group, for example benzyl group, may be removed by hydrogenolysis using a catalyst, such as Raney nickel, palladium-carbon or palladium hydroxide-carbon. The amount of catalyst used may usually be about 1 to 20% by weight based on the benzyl ether. Generally, this reaction is preferably carried out in a solvent medium, such as methanol, ethanol, tetrahydrofuran, acetic acid and the like. The amount of medium used may be about 1 to 5 ml per g of the benzyl ether. This reaction is carried out under hydrogen atmosphere, usually at a hydrogen pressure of about 1 to 10 atm, preferably about 1 to 3 atm. Further, this reaction may generally be carried out at about –10 to 100° C., preferably for about 1 to 24 hours.

Acetyl group may be removed by hydrolysis of an acetic acid ester using a base, such as sodium carbonate, potassium carbonate, sodium hydroxide, potassium hydroxide or the like. The amount of base used may usually be about 0.1 to 10 times by mole based on the acetic acid ester. Generally, this reaction is preferably carried out in methanol, ethanol, tetrahydrofuran or 1,4-dioxane, or a mixed medium thereof with water. The amount of medium used may usually be about 1 to 5 ml per g of the acetic acid ester. In general, this reaction is preferably carried out at about –20 to 100° C., particularly about 0 to 50° C., for about 1 to 5 hours.

Protecting groups for amino groups may be deprotected by known methods described in literatures (for example, T. W. Greene, P. G. M. Wuts, et al., *Protective Groups in Organic Synthesis*, Wiley-Interscience Publication). For example, benzyl group may be removed by hydrogenolysis using a catalyst, such as Raney nickel, palladium-carbon, palladium hydroxide-carbon and the like. The amount of catalyst used may usually be about 1 to 20% by weight based on the protected amine. Generally, this reaction is preferably carried out in a solvent medium, such as methanol, ethanol, tetrahydrofuran, acetic acid or the like. The amount of medium used may be about 1 to 50 ml per g of the protected amine. This reaction is carried out under a hydrogen atmosphere, generally at a hydrogen pressure of about 1 to 10 atm, preferably at about 1 to 3 atm.

Generally, this reaction is preferably carried out at about –10 to 100° C. for about 1 to 24 hours. When $R^{11}$ is a halogen atom, then the deprotection should be performed according to the methods described in M. Koreeda, et al., *J. Org. Chem.*, 49, p. 2081 (1984) or S. Gubert, et al., *Synthesis*, 4, p. 318 (1991).

Acetyl groups may be removed in a similar manner as in the above-mentioned hydrolysis of acetic acid esters under basic conditions. When an acyl group is used as a protecting group for amino groups, the hydrolysis reaction may be generally carried out at room temperature to about 100° C.

The removal of protecting groups for hydroxyl and amino groups may be carried out either sequentially in multiple steps or simultaneously in a single step. For example, if $R^{11}$ is a benzyloxy group and $R^2$ is a benzyl group, the deprotection can be conducted under the same conditions and is preferably carried out simultaneously in a single step. If $R^{11}$ is a benzyloxy group and $R^2$ is an acetyl group, the acetyl group in $R^2$ may be deprotected followed by deprotection of the benzyl group in $R^{11}$. However, the order of these deprotection reactions is not limited thereto and may be appropriately chosen depending upon the physical properties of the compound and the like. The conditions for each of the deprotection reactions are as previously mentioned. Also, reference may be made to the methods described in JP-A-9-249623.

Examples of the compound of the formula (1) include:

2-[N-[2-(9H-carbazol-2-yloxy)ethyl]]amino-1-[(3-methylsulfonylamino)phenyl]ethanol, 2-[N-[2-(9H-carbazol-2-yloxy)ethyl]]amino-1-[(4-hydroxy-3-methylsulfonylamino)phenyl]ethanol, 2-[N-[2-(9H-carbazol-2-yloxy)ethyl]]amino-1-[(4-chloro-3-methylsulfonylamino)phenyl]ethanol, 2-[N-[2-(9H-carbazol-2-yloxy)ethyl]]amino-1-[(4-bromo-3-methylsulfonylamino)phenyl]ethanol, and salts thereof. Particularly preferred examples are those compounds in their R-form.

The process for the preparation of the compound of the formula (1) according to the present invention will be hereinbelow described in more detail.

Thus, a compound of the formula (7) is reduced to give a halohydrin of the formula (6). Then, an epoxy compound of the formula (5) is formed under alkaline conditions and reacted with a compound of the formula (9) to give an amino alcohol of the formula (4). The nitro group is then reduced to give an aniline derivative of the formula (3) and subsequently reacted with a sulfonating agent to give an amino alcohol of the formula (2). Finally, the protected groups are deprotected in a single step or stepwise in multiple steps to give a compound of the formula (1).

The compound of the formula (7) can be obtained by nitrating compound of the formula (10):

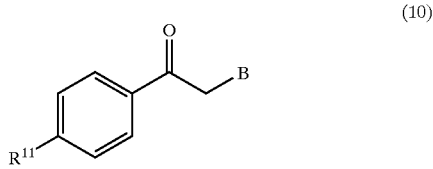

(10)

wherein $R^{11}$ and B are as above defined, with a known nitrating agent, such as mixed acid, fuming nitric acid, concentrated sulfuric acid-potassium nitrate or acetic anhydride-potassium nitrate. This nitration can be performed in a similar manner to the reaction described in, for example, H. G. Garg, et al., *J. Chem. Soc. C*, 4, p. 607 (1969).

The compound of the formula (10) wherein $R^{11}$ is a hydrogen atom may be commercially available product (Aldrich), which can be used as it is. The compounds wherein $R^{11}$ is a protected hydroxyl group may be obtained by protecting a hydroxyl group of commercially available products (Karl Industry) in the above-mentioned method. Those wherein $R^{11}$ is a halogen atom may be obtained by chlorinating or brominating the a position relative to the ketone group in commercially available 4'-haloacetophenones (Aldrich). The chlorination and bromination may be carried out using any conventional chlorinating and brominating agents, respectively. Examples of the chlorinating agent may include, for example, chlorine, sulfuryl chloride, seleninyl chloride, hypochlorous acid, N-chlorosuccinimide, cupric chloride, quaternary ammonium polychloride, hexachloro-2,4-cyclohexadiene, the complex of 3-chloroperbenzoic acid-hydrogen chloride-N,N-dimethylformamide and the like. Examples of the brominating agent may include, bromine, N-bromosuccinimide, cupric bromide, and quaternary ammonium polybromide and the like.

The compound of the formula (7) may also be obtained by chlorinating or brominating the a position relative to the ketone group in a compound of the formula (8):

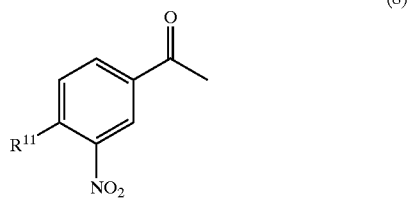

(8)

wherein $R^{11}$ is as defined above. The chlorination and bromination may be carried out using such a chlorinating and brominating agent, respectively, as mentioned above.

The compound of the formula (8) wherein $R^{11}$ is a hydrogen or chlorine atom may be commercially available product (ICN Pharmaceuticals), which can be used as it is. Those compounds wherein $R^{11}$ is a halogen atom other than chlorine may be obtained by nitrating commercially available 4'-haloacetophenones (Aldrich) under similar conditions to those as set forth above. Those wherein $R^{11}$ is a protected hydroxyl group may be obtained by protecting the hydroxyl group of commercially available 4'-hydroxy-3'-nitroacetophenone (Aldrich) in the above-mentioned method.

The compound of the formula (6) may be obtained by reducing the compound of the formula (7) with a known reducing agent. Examples of the reducing agent may include, for example, sodium borohydride, aluminium isopropoxide, trialkylsilane and the like and metal hydrides, such as sodium borohydride, are preferred. The amount of sodium borohydride added may generally be about 0.5 to 3 times by mole based on the compound of the formula (6). In general, this reaction may preferably be carried out in a lower alcohol medium. The lower alcohol medium may include methanol, ethanol, 2-propanol and the like. The lower alcohol may be preferably ethanol. The amount of the lower alcohol used may generally be about 1 to 5 ml per g of the compound of the formula (7). If solubility is low, it may usually be preferred that about 1 to 5 ml of tetrahydrofuran as a cosolvent is added per g of the compound of the formula (7). Preferably, this reaction is carried out usually at −20 to 50° C., particularly 0° C. to room temperature, for about 1 to 5 hours.

Further, when either R or S optical isomer in respect of *1 in the formula (6) is to be obtained, asymmetric reduction may be conducted using a hydrogen donor compound in the presence of an asymmetric reduction catalyst known from various literatures, for example, Achiwa, et al., *Chem. Pharm. Bull.*, 43, p. 748 (1995) or Noyori, et al., *J. Am. Chem. Soc.*, 118, p. 2521 (1996).

WO 97/20789 and JP-A-9-157196 have described various methods for synthesizing an optically active alcohol from a ketone. The above mentioned asymmetric reduction catalyst may be preliminarily prepared from a metal complex and a ligand prior to the asymmetric reduction reaction. Alternatively, the catalyst may be prepared from a metal complex and a ligand in situ in a reaction system. The metal complex comprises a variety of transition metals and ligand (s). Particularly suitable transition metal complexes may be represented by, for example, $MX_mL_n$ wherein M is a transition metal of the Group VIII, such as iron, cobalt, nickel, ruthenium, rhodium, iridium, osmium, palladium, platinum and the like, X represents a hydrogen or halogen atom, or a carboxyl group, a hydroxyl group, an alkoxy group or the like, L represents a neutral ligand, such as an aromatic compound or an olefin compound, and m and n represent integers.

Among the transition metals in these transition metal complexes, ruthenium is desirable. When said neutral ligand is an aromatic compound, it may include a monocyclic aromatic compound. The aromatic compound may optionally be substituted with one or more substituents, such as, for example, a hydrogen atom, a saturated or unsaturated hydrocarbon group, an allyl group, and a functional group containing heteroatom(s), at any position(s). More specifically, the substituents may include alkyl groups, such as methyl, ethyl, propyl, i-propyl, butyl, t-butyl, pentyl, hexyl and heptyl; cycloalkyl groups, such as cyclopropyl, cyclobutyl, cyclopentyl and cyclohexyl; unsaturated hydrocarbon groups, such as benzyl, vinyl and allyl; and functional groups containing heteroatom(s), such as hydroxyl, alkoxy and alkoxycarbonyl groups.

Specific examples of the metal complexes may include the following 1,2-diphenylethylenediamine-ruthenium complexes, for example:

[(S,S)-N-(p-toluenesulfonyl)-1,2-diphenylethylenediamine] benzene ruthenium complex,
[(S,S)-N-(p-toluenesulfonyl)-1,2-diphenylethylenediamine] (p-cymene)ruthenium complex,
[(S,S)-N-methanesulfonyl-1,2-diphenylethylenediamine] benzene ruthenium complex,
[(S,S)-N-trifluoromethanesulfonyl-1,2-diphenylethylenediamine]mesitylene ruthenium complex,
[(S,S)-N-methanesulfonyl-1,2-diphenylethylenediamine](p-cymene)ruthenium complex,
[(S,S)-N-benzenesulfonyl-1,2-diphenylethylenediamine](p-cymene)ruthenium complex,
[(S,S)-N-(p-fluorobenzenesulfonyl)-1,2-diphenylethylenediamine](p-cymene)ruthenium complex,
[(S,S)-N-trifluoromethanesulfonyl-1,2-diphenylethylenediamine](p-cymene)ruthenium complex,
[(S,S)-N-(p-methoxybenzenesulfonyl)-1,2-diphenylethylenediamine](p-cymene)ruthenium complex,
[(S,S)-N-methanesulfonyl-1,2-diphenylethylenediamine] mesitylene ruthenium complex,
[(S,S)-N-(p-toluenesulfonyl)-1,2-diphenylethylenediamine] mesitylene ruthenium complex,
hydride-[(S,S)-N-(p-toluenesulfonyl)-1,2-diphenylethylenediaamine]benzene ruthenium complex,
hydride-[(S,S)-N-(p-toluenesulfonyl)-1,2-diphenylethylenediamine](p-cymene)ruthenium complex,
hydride-[(S,S)-N-methanesulfonyl-1,2-diphenylethylenediamine]benzene ruthenium complex,
hydride-[(S,S)-N-trifluoromethanesulfonyl-1,2-diphenylethylenediamine]mesitylene ruthenium complex,
hydride-[(S,S)-N-methanesulfonyl-1,2-diphenylethylenediamine](p-cymene)ruthenium complex,
hydride-[(S,S)-N-benzenesulfonyl-1,2-diphenylethylenediamine](p-cymene)ruthenium complex,
hydride-[(S,S)-N-(p-fluorobenzenesulfonyl)-1,2-diphenylethylenediamine](p-cymene)ruthenium complex,
hydride-[(S,S)-N-trifluoromethanesulfonyl-1,2-diphenylethylenediamine](p-cymene)ruthenium complex,
hydride-[(S,S)-N-(p-methoxybenzenesulfonyl)-1,2-diphenylethylenediamine](p-cymene)ruthenium complex,
hydride-[(S,S)-N-methanesulfonyl-1,2-diphenylethylenediamine]mesitylene ruthenium complex,
hydride-[(S,S)-N-(p-toluenesulfonyl)-1,2-diphenylethylenediamine]mesitylene ruthenium complex,
chloro-[(S,S)-N-(p-toluenesulfonyl)-1,2-diphenylethylenediamine]benzene ruthenium complex,
chloro-[(S,S)-N-(p-toluenesulfonyl)-1,2-diphenylethylenediamine](p-cymene)ruthenium complex,
chloro-[(S,S)-N-methanesulfonyl-1,2-diphenylethylenediamine]benzene ruthenium complex,
chloro-[(S,S)-N-trifluoromethanesulfonyl-1,2-diphenylethylenediamine]mesitylene ruthenium complex,
chloro-[(S,S)-N-methanesulfonyl-1,2-diphenylethylenediamine](p-cymene)ruthenium complex,
chloro-[(S,S)-N-benzenesulfonyl-1,2-diphenylethylenediamine](p-cymene)ruthenium complex,
chloro-[(S,S)-N-(p-fluorobenzenesulfonyl)-1,2-diphenylethylenediamine)](p-cymene)ruthenium complex,
chloro-[(S,S)-N-trifluoromethanesulfonyl-1,2-diphenylethylenediamine](p-cymene)ruthenium complex,
chloro-[(S,S)-N-(p-methoxybenzenesulfonyl)-1,2-diphenylethylenediamine](p-cymene)ruthenium complex,
chloro-[(S,S)-N-methanesulfonyl-1,2-diphenylethylenediamine]mesitylene ruthenium complex, and
chloro-[(S,S)-N-(p-toluenesulfonyl)-1,2-diphenylethylenediamine]mesitylene ruthenium complex. Any of these metal complexes can be used as the catalyst in the present invention as it is.

It is also known to use in the asymmetric reduction those catalysts which are obtained by reacting the following rhodium complexes with the following chiral phosphine ligands. For example, the rhodium complexes, such as

[Rh(nbd)$_2$]ClO$_4$ wherein nbd means norbornadiene, [Rh(nbd)Cl]$_2$, and
[Rh(cod)Cl]$_2$ wherein cod means cycloocta-1,5-diene, are known. Examples of the chiral phosphine ligands may include, for example:
(2R,3R)-2,3-bis(diphenylphosphino)-bicyclo[2,2,1]hept-5-ene [abbreviated as (R, R)-NORPHOS],
(R)-5,5'-dimethoxy-4,4',6,6'-tetramethyl-2-diphenylphosphino-2'-dicyclohexylphosphino-1,1'-biphenyl [abbreviated as (R)-MOC-BIMOP],
(R)-5,5'-dimethoxy-4,4',6,6'-tetramethyl-2,2'-bis(dicyclohexylphosphino)-1,1'-biphenyl [abbreviated as (R)-Cy-BIMOP],
(2S,3S)-1,4-bis[bis(4-methoxy-3,5-dimethylphenyl)phosphino]-2,3-O-isopropylidene-2,3-butanediol [abbreviated as (S,S)-MOD-DIOP],
(2S,3S)-1,4-bis(diphenylphosphino)-2,3-O-isopropylidene-2,3-butanediol [abbreviated as (S,S)-DIOP],
(2S,3S)-1-diphenylphosphino-4-dicyclohexylphosphino-2,3-O-isopropylidene-2,3-butanediol [abbreviated as (S,S)-DIOCP],
(R)-1-[(S)-1',2-bis(diphenylphosphino)ferrocenyl]ethanol [abbreviated as (R)-(S)-BPPFOH],
(S)-1-[(S)-1',2-bis(diphenylphosphino)ferrocenyl]ethanol [abbreviated as (S)-(S)-BPPFOH],
(1S,2S)-1-(diphenylphosphino)-2-[(diphenylphosphino)methyl]cyclopentane [abbreviated as (S,S)-PPCP], and
(1R,2R)-1-(dicyclohexylphosphino)-2-[(diphenylphosphino)methyl]cyclopentane [abbreviated as (R,R)-CPCP].

In another preferred process, the compound of the formula (7) may be reduced with a borane in the presence of a catalytic amount of a chiral auxiliary agent (cis-1-amino-2-indanol or cis-1-amino-2-tetralol). This reaction may be conducted according to the method described in R. Hett, et al., *Org. Process Res, Dev.*, 2, p. 96 (1998), or *Tetrahedron Letters*, 39, p. 1705 (1998).

An additional preferred method may be asymmetrical reduction using a stoichiometric amount of a compound of the following formula (12):

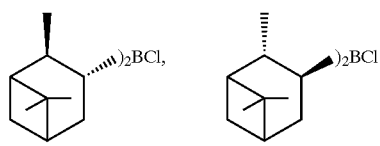

(diisopinocampheylchloroborane) as an asymmetric reducing agent. This reaction may be conducted according to the method described in H. C. Brown, *J. Org. Chem.*, 54, p. 1577 (1989).

When the asymmetric reduction is carried out in the presence of the known asymmetric reducing catalyst or chiral auxiliary agent, it can be all appropriately selected after it has preliminarily been proved that the asymmetric reduction preferably proceeds in the present invention. Possibly, however, such selection may be limited in some cases. For example, a particularly preferred example may be a catalyst represented by the following formula (14):

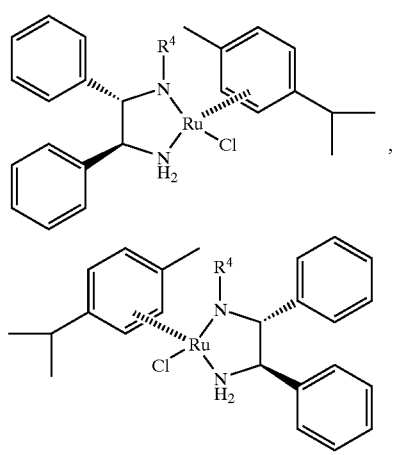

wherein $R^4$ represents p-toluenesulfonyl or methanesulfonyl group, which may be obtained by reacting a ruthenium complex $[RuCl_2(\text{p-cymene})]_2$ with a chiral ethylenediamine ligand represented by the following formula (13):

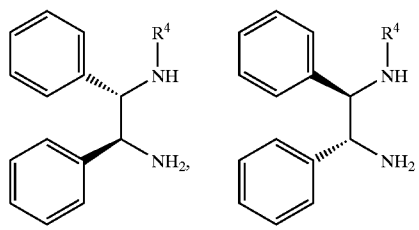

wherein $R^4$ is as defined above. Thus, a compound of the formula (7) may be asymmetrically reduced in the presence of said ruthenium complex and an appropriate hydrogen donor compound to give an optically active compound of the formula (6).

Particularly preferred examples of the compound of the formula (7) include those wherein B is a chlorine atom. This reaction may be conducted according to the method described in Noyori et al., *J. Am. Chem. Soc.*, 118, p. 2521 (1996).

When the compound of the formula (7) is asymmetrically reduced by a 1,2-diphenylethylenediamine ruthenium complex, the compound of the formula (7) and a hydrogen donor compound may be reacted in the presence of said catalyst. Generally, the catalyst may be added in an amount of about 0.001 to 1 time by mole based on the compound of the formula (7). The hydrogen donor compound may include hydrogen gas, alcoholic compounds, such as methanol, ethanol, 1-propanol and 2-propanol, complexes of formic acid with an amine, such as triethylamine or N,N-diisopropylethylamine, unsaturated hydrocarbons having a partially saturated carbon bond, such as tetralin and decalin, heterocyclic compounds, hydroquinones, phosphorous acid, and the like. Particularly preferred examples include complexes of formic acid and triethylamine in a mixing ratio of 1/100 to 100/1. Generally, the amount of the formic acid-triethylamine complex added may be such that the amount by equivalent of formic acid is about 1 to 10 times by mole based on the compound of the formula (7). Preferably, the reaction is carried out in a medium. The medium may include, for example, alcohol medium, such as methanol, ethanol and 2-propanol; acetone medium, such as acetone and 2-butanone; ester medium, such as methyl acetate, ethyl acetate and butyl acetate; aromatic medium, such as toluene and xylene; halogen-containing medium, such as dichloromethane and chloroform; formamide medium, such as N,N-dimethylformamide and N,N-dimethylacetamide; sulfoxide medium, such as dimethylsulfoxide and sulfolane; nitrile medium, such as acetonitrile; and ether medium, such as diethyl ether, tetrahydrofuran and 1,4-dioxane. Alcoholic medium, such as 2-propanol, are particularly preferred.

The amount of the reaction medium is generally about 0.1 to 100% by weight based on the compound of the formula (7). The reaction temperature may be in the range of about −30 to 50° C., preferably about −20° C. to room temperature, where a good optical purity may be provided. The reaction time may be in the range of about 0.5 to 10 days, preferably about 1 to 3 days.

Further, the presence of a base is preferred in the reaction. The base may include, for example, potassium hydroxide, sodium hydroxide, lithium hydroxide, potassium methoxide and potassium t-butoxide with potassium hydroxide, sodium hydroxide or lithium hydroxide being preferred.

The above-mentioned asymmetric reduction reaction using a complex of formic acid and triethylamine as a hydrogen donor source is very simple; i.e., a haloketone of the formula (7), a ruthenium catalyst of the formula (14), and a complex of formic acid and triethylamine is merely mixed in a medium, requiring no special reaction vessel. Thus, it is appreciated that this method is preferable since it reduces a cost and simplifies complicated processes.

When the asymmetric reduction uses cis-1-amino-2-indanol or cis-1-amino-2-tetralol, the compound of the formula (7) may be reduced with a borane in the presence of this chiral auxiliary agent. Generally, the chiral auxiliary agent is used in an amount of about 0.05 to 0.3 time by mole based on the compound of the formula (7). The borane is generally used in an amount of about 0.5 to 1 time by mole based on the compound of the formula (7). The reaction medium used may be aromatic medium, such as toluene and xylene; ether medium, such as diethyl ether, tetrahydrofuran and 1,4-dioxane; halogen-containing medium, such as dichloromethane and chloroform; and saturated aliphatic medium, such as pentane and hexane. Preferably, ether medium, such as tetrahydrofuran, are used. The reaction temperature may be in the range of about −50 to 50° C. In particular, about −20° C. to room temperature is preferred. The reaction time is usually in the range of about 1 to 24 hours, preferably about 2 to 10 hours.

In the asymmetric reduction using diisopinocampheylchloroborane, the compound of the formula (7) may be reduced with diisopinocampheylchloroborane of the formula (12), which is usually used in an amount of about 1 to 10 times by mole, preferably about 1 to 3 times by mole, based on the compound of the formula (7). Example of the reaction medium used may include aromatic medium, such as toluene and xylene; ether medium, such as diethyl ether, tetrahydrofuran and 1,4-dioxane; halogen-containing medium, such as dichloromethane and chloroform; and saturated aliphatic medium, such as pentane and hexane. Preferably, ether medium, such as tetrahydrofuran, are used. The reaction temperature is generally in the range of about −50 to 50° C., preferably about −20 to 0° C. In general, lower temperatures often provide higher optical yields and thus preferred. The reaction time is in the range of about 1 to 24 hours, preferably about 5 to 15 hours.

In the practice of the above-mentioned asymmetric reduction, it should be verified that the asymmetric reaction preferably proceeds in the present invention and said alcohol has a desired configuration before an asymmetric reducing catalyst or chiral auxiliary agent having required configuration should be appropriately selected.

Alternatively, the compound of the formula (5) may be obtained by direct oxidation of 3-nitrostyrene in the presence of a catalyst. Thus, commercially available 3-nitrostyrene (Aldrich) may be oxidized using an optically active porphyrin complex by the method described in, for example, J. P. Collman et al., *J. Am. Chem. Soc.*, 121, pp. 460–461 (1999), to provide a desired optically active compound of the formula (5).

The compound of the formula (5) is excellent in crystallization and is useful intermediate, which not only can be purified by recrystallization but also have utility in improvement of optical purity. The compound of the formula (5) is obtained from the compound of the formula (6) by conventionally known methods. For example, the reaction may be carried out in an alcohol medium, such as methanol or ethanol, or an acetone medium, such as acetone or 2-butanone, using an alkali in an amount of about 1 to 5 times by mole based on the compound of the formula (6), at room temperature to the reflux temperature of the medium used. The alkali may include sodium carbonate, potassium carbonate, sodium hydroxide, potassium hydroxide and the like.

The compound of the formula (4) is a novel and may be obtained by reacting the compound of the formula (5) with the compound of the formula (9). This reaction may be carried out in a conventional medium, such as, for example, methanol, ethanol, 2-propanol, ethyl acetate, tetrahydrofuran, 1,4-dioxane, benzene, toluene, N,N-dimethylformamide, N,N-dimethylacetamide, dimethylsulfoxide, sulfolane, dichloromethane or chloroform. In particular, 2-butanol is preferably used. The medium used may be usually in the range of about 5 to 100 ml per g of the compound of the formula (5). The compound of the formula (5) and the compound of the formula (9) are often used in equimolar amounts. Preferably, an excess amount of the compound of the formula (9) is used. This reaction may be preferably carried out usually in the range of room temperature to about 150° C., particularly about 50 to 120° C. The reaction time may be appropriately chosen depending upon the reaction conditions and may generally be terminated at a maximum yield.

The compound of the formula (9) may be obtained by protecting a known primary amine compound NH$_2$—CH$_2$CH$_2$—OA', which may be synthesized by the method described in JP-A-9-249623, with a protecting group R$^2$. Thus, when R$^2$ is a benzyl group, either reductive alkylation by benzaldehyde or alkylation by a benzyl halide, benzyl sulfonate or the like may be used. For example, in the reductive alkylation, benzaldehyde may be generally added in an amount of 1 to 1.5 times by mole based on the primary amine. Preferably, this reaction is generally carried out in a medium, such as tetrahydrofuran, water, methanol or ethanol, with methanol being particularly preferred. The amount of the medium used may be generally in the range of about 10 to 100 ml per g of primary amine. In general, this reaction is preferably carried out at room temperature, for example, for about 3 to 10 hours.

Generally, this reaction is preferably carried out in the presence of a catalyst of the platinum group. Preferably, the platinum group catalyst may be, for example, platinum oxide. The amount of the platinum group catalyst used may usually be in the range of about 0.01 to 0.1 time by mole based on the primary amine. Further, this reaction is carried out under a hydrogen atmosphere and the hydrogen pressure may be usually in the range of about 1 to 10 atm, particularly about 1 to 3 atm.

Alternatively, the compound of the formula (9) may be synthesized in two steps from A'—OH. Thus, a known compound A'—OH is reacted with 1,2-dibromoethane to give a compound of the formula (11):

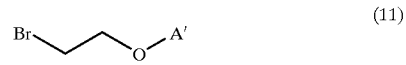

and further reacted with an amine NH$_2$—R$^2$ wherein R$^2$ is a substituted benzyl group.

The reaction of A'—OH with 1,2-dibromoethane may be carried out in a medium, generally in the presence of a base, at room temperature to the reflux temperature of the selected medium. Preferably, 1,2-dibromoethane is used in an amount of 3 to 15 times by mole based on A'—OH. The medium used includes N,N-dimethylformamide, N,N-dimethylacetamide, 2-butanone, acetonitrile, diglyme, tetrahydrofuran and the like. The base may be potassium carbonate, sodium carbonate, sodium hydroxide, potassium hydroxide, triethylamine, pyridine, sodium hydride, sodium methoxide or the like, which is preferably used in an amount of 1 to 5 times by mole based on A'—OH. Generally, the amount of the medium used may be in the range of about 5 to 100 ml per g of A'—OH. In general, this reaction may be preferably carried out at about 60 to 90° C., for example, for about 3 to 24 hours.

The reaction of a compound of the formula (11) with NH$_2$—R$^2$ may be carried out either in a medium or in the absence of medium at about 60 to 100° C. The amount of NH$_2$—R$^2$ used may be in the range of 2 to 10 times by mole based on the compound of the formula (11). The medium used may include N,N-dimethylformamide, N,N-dimethylacetamide, dimethylsulfoxide, 2-propanol and the like.

A'—OH may be obtained by the methods described in JP-A-9-249623 (WO 97/25311) and WO 99/01431. For example, 2-hydroxycarbazole is commercially available (Aldrich) and this product may be conveniently and preferably used.

As stated above, the compound of the formula (9) may be prepared from A'—OH in two steps, shows good crystallinity, and may be obtained by mere filtration without complicated processes. Further, after the reaction with the compound of the formula (5), the excess compound of the formula (9) can be recovered and recycled, reducing cost and avoiding complicated processes. Thus, it is appreciated that this is a preferable method.

The compound of the formula (3) is novel and this compound may be obtained by reducing the compound of the formula (4) by known methods. Preferably, a reducing agent is appropriately selected depending upon the nature of the substituent $R^{11}$. For example, when $R^{11}$ is a hydrogen atom or a benzyloxy group, the reduction may be carried out with a metal hydride, such as litium aluminium hydride or borane, a metal, such as tin, iron, titanium or zinc, a chloride of the metal, sodium sulfide, or the like. It may be particularly preferred to carry out the reduction with hydrogen in the presence of a platinum group catalyst, such as platinum oxide. Generally, platinum oxide is used in an amount of about 0.001 to 0.1 times by mole, preferably about 0.005 to 0.03 times by mole, based on the compound of the formula (4). In general, this reaction is preferably carried out in a medium, such as methanol, ethanol, 2-propanol, tetrahydrofuran, ethyl acetate, acetic acid or water, with ethanol being particularly preferred.

Generally, the amount of the medium used may be about 1 to 50 ml per g of the compound of the formula (4). This reaction is carried out under a hydrogen atmosphere, generally at a hydrogen pressure of 1 to 10 atm, preferably about 1 to 3 atm, for example, for 0.5 to 5 hours. When $R^{11}$ is a halogen atom, the reduction may be carried out with sodium borohydride in the presence of a transition metal complex, a metal, such as tin, iron, titanium or zinc, a chloride of the metal, sodium sulfide, or the like. Reduction with sodium borohydride in the presence of bis(2,4-pentanedionato) copper may be particularly preferred. This reaction may be carried out according to the method described in K. Hanaya, et al., *J. Chem. Soc. Perkin I*, p. 2409 (1979).

The compound of the formula (2) may be obtained by reacting the compound of the formula (3) with a sulfonating agent in the presence of a base. The sulfonating agent may be sulfonic acid chloride or anhydride substituted with $R^3$ wherein $R^3$ is as defined above. The base includes organic tertiary amines, such as triethylamine, N,N-diisopropylethylamine, pyridine and 4-dimethylaminopyridine, and inorganic bases, such as sodium hydroxide, potassium hydroxide, sodium carbonate, potassium carbonate and sodium hydrogencarbonate. Pyridine and sodium hydrogencarbonate may be particularly preferred for sulfonic acid chloride and sulfonic acid anhydride, respectively. The amount thereof used may generally be in the range of about 1 to 10 times by mole, while the base may preferably serve as a medium as well. Preferably, this reaction is carried out in a medium, such as pyridine, tetrahydrofuran, 1,4-dioxane, dichloromethane, chloroform, ethyl acetate, benzene, toluene or acetone with tetrahydrofuran being particularly preferred. The amount of the medium used may generally be in the range of about 1 to 50 ml per g of the compound of the formula (3). Generally, this reaction is preferably carried out at about 0 to 50° C., for example, for 0.5 to 5 hours.

The sulfonic acid chlorides ($R^3SO_2Cl$) may be commercially available (Aldrich) and unavailable ones can be obtained by chlorinating $R^3SO_3Na$ with a known chlorinating agent. The chlorinating agent may be, for example, thionyl chloride, phosphorus pentachloride or the like. The sulfonic acid anhydrides ($R^3SO_2)_2O$ may be commercially available (Aldrich) and unavailable ones can be obtained by dehydrating sulfonic acid with phosphorus pentaoxide, reacting sulfonic acid with dicyclohexylcarbodiimide (DCC), or reacting sulfonic acid with thionyl chloride or carboxylic acid chloride.

Subsequently, the protecting groups may be removed in a single step or stepwise by the above-mentioned methods to give the compound of the formula (1).

In each step of the synthesizing route set forth above, the product is preferably purified by a known purifying means, such as column chromatography and the like. However, the compounds of the formulae (7) and (5) are relatively good in crystallinity and can be used in the following reaction step after being subjected to a simple recrystallizing treatment without complicated processes. Therefore, the present process, which can save cost and avoid a complication, is a preferred process. In addition, the present process is also preferred in that each reaction step results in good yield.

In the above disclosed synthesis route, the asymmetric reduction of the carbonyl group in the compound of the formula (7) is particularly characteristic and the resulting reduced compound is a useful intermediate.

As previously stated, the compound of the formula (1) may exist in either form of two different optical isomers. The process disclosed by the present invention may provide a racemic mixture and, if necessary, an optical isomer. The described reactions above do not change stereochemistry involved. If a mixture of two isomers obtained is to be resolved into respective optical isomers, they can be resolved by converting them into addition salts with an optically active acid, such as camphorsulfonic acid, mandelic acid or a substituted mandelic acid, and subjecting the salts to any appropriate method, such as fractional crystallization. The fractional crystallization may be carried out using an appropriate solvent, preferably a lower alcohol, for example, methanol, ethanol, 2-propanol or any mixture thereof. Each pair of enantiomers can be resolved into respective pure isomers by formation of diastereomer salts, chromatography using an optically active column, or any other means.

When either of the starting material is optically active, the resulting mixture of diastereomers thus obtained is resolved by the above-mentioned method. This resolution may be applied to the compound of the formula (1) or the intermediate amino alcohol (4), (3) or (2) obtained in the respective steps. By resolving and purifying optically active isomers, it is possible to use only isomers of higher activities and, therefore, improve the effects or eliminate side-effects, providing preferable drugs.

The compounds of the formulae (1), (2), (3) and (4) in the present invention encompass salts thereof, including any known salts, for example, hydrochloride, hydrobromide, sulfate, hydrogensulfate, dihydrogenphosphate, citrate, maleate, tartrate, fumarate, gluconate, methanesulfonate, and addition salts with an optically active acid, such as camphorsulfonic acid, mandelic acid or a substituted mandelic acid. Pharmaceutically acceptable salts are particularly preferred. When the compounds of the formulae (1), (2), (3) and (4) are converted into their salts, they may be dissolved in an alcohol, such as methanol or ethanol and one to several equivalents of an acid component are added to give their acid addition salts. The acid component used may include any pharmaceutically acceptable inorganic or organic acids, such as hydrochloric acid, hydrobromic acid, sulfuric acid, hydrogensulfuric acid, dihydrogenphosphoric acid, citric acid, maleic acid, tartaric acid, fumaric acid, gluconic acid, methanesulfonic acid.

Chapter 2

The halohydrin of the formula (6) shown in Chapter 1 have been obtained by, for example, α-chlorination of acetophenone derivative of the formula (16). For example, this chlorination is described in Paulo, et al., *Magnetic Reso.*

Chem., 25, p. 179 (1987), or Hach, et al., *Collect, Czech. Chem. Commun.*, 28, p. 266 (1963), that is, chlorination by sulfuryl chloride in chloroform. JP-A-8-277240 and Arturo, et al., *Synth. Commun.*, 26, p. 1253 (1996) disclose use of sulfuryl chloride in methylene chloride and methanol. Thus, the α-chlorination of acetophenone derivatives by sulfuryl chloride has been done in a halogen-containing solvent.

Recently, however, environmental problems have become of great interest and atmospheric pollution and waste water contamination by halogen-containing solvents have seriously been regulated. Chlorination using a halogen-containing solvent in an industrial production level is problematic. Therefore, there is a need for the use of solvents other than the halogen-containing solvents.

To solve these problems, the present inventors have investigated various solvents and succeeded in establishing a preferable synthesis route providing a high yield with easy operations and without using a halogen-containing solvent. Thus, the present invention has been completed.

That is, the present invention is a process for the preparation of a compound of the formula (1):

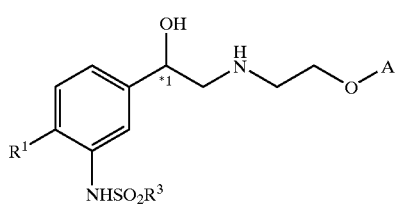

(1)

wherein $R^1$ represents a hydrogen or halogen atom, $R^3$ represents a lower alkyl group or a benzyl group, *1 represents an asymmetric carbon atom, and A represents one of the following groups:

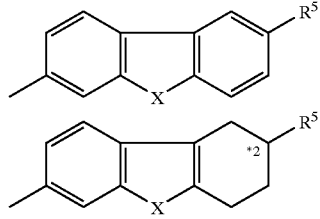

wherein X represents NH, O or S, $R^5$ represents a hydrogen atom, or a hydroxyl, amino or acetylamino group, and *2 represents an asymmetric carbon atom when $R^5$ is not a hydrogen atom,
said process comprising:
chlorinating a compound of the formula (18):

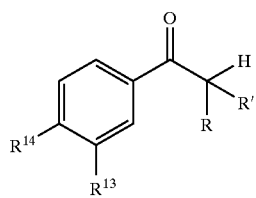

(18)

wherein $R^{14}$ represents a hydrogen or halogen atom, $R^{13}$ represents nitro, and both R and R' represent a hydrogen atom, with sulfuryl chloride in an ether solvent, to give a compound of the formula (19):

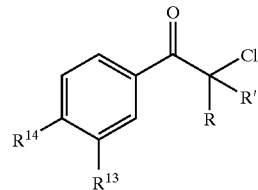

(19)

wherein $R^{13}$, $R^{14}$, R and R' are as defined above; and,
reducing the chlorinated compound to give a halohydrin of the formula (6):

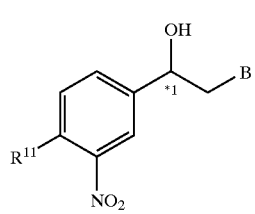

(6)

wherein $R^{11}$ represents a hydrogen atom or halogen atom, B represents a chlorine atom, and *1 is as defined above; and,
converting the halohydrin under alkaline conditions into an epoxy compound of the formula (5):

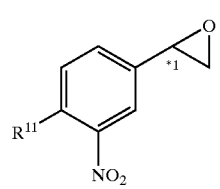

(5)

wherein $R^{11}$ and *1 are as defined above; and,
reacting the epoxy compound with a compound of the formula (9):

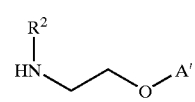

(9)

wherein $R^2$ represents an amino-protecting group, and A' represents one of the following groups:

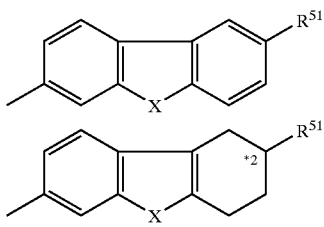

wherein X represents NH, O or S, $R^{51}$ represents a hydrogen atom, a protected hydroxyl group, a protected amino group or an acetylamino group, and *2 represents an asymmetric carbon atom when $R^{51}$ is not a hydrogen atom, to give an amino alcohol of the formula (4):

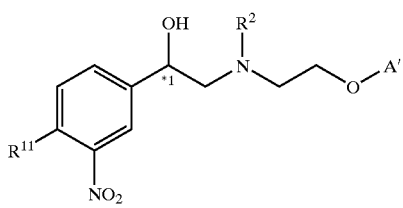
(4)

wherein $R^{11}$, $R^2$, A' and *1 are as defined above; and, reducing the nitro group to give an aniline derivative of the formula (3):

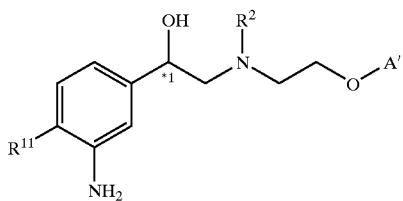
(3)

wherein $R^{11}$, $R^2$, A' and *1 are as defined above; and, reacting the aniline derivative with a sulfonating agent to give an amino alcohol of the formula (2):

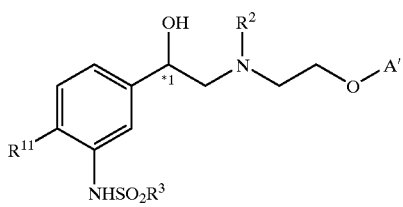
(2)

wherein $R^3$, $R^{11}$, $R^2$, A' and *1 are as defined above; and then, simultaneously or sequentially removing the protecting groups to give the compound of the formula (1).

Further, there has been found a process for the preparation of an α-chloroacetophenone derivative of the formula (17):

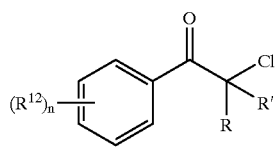
(17)

wherein n represents 1 to 5, $R^{12}$ represents a hydrogen or halogen atom, or acyloxy, acylamino, $NR^6SO_2R^3$, cyano, trifluoromethyl or nitro, and when n is 2 or more, $R^{12}$ represents same or different substituents as defined above, and R and R' may be same or different from each other and represent a hydrogen atom, a lower alkyl group or an aryl group, and wherein $R^6$ represents a hydrogen atom or an amino-protecting group, and $R^3$ represents a lower alkyl group or a benzyl group, said process comprising:
chlorinating a compound of the formula (16):

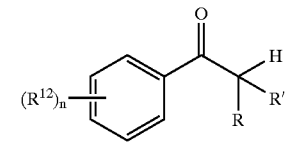
(16)

wherein n, $R^{12}$, R and R' are as defined above, with sulfuryl chloride in an ether solvent to give the compound of the formula (17), which process can be generally applicable to α-chlorination of acetophenone derivatives.

Further, the present invention is a process for the preparation of an α-chloroacetophenone derivative of the formula (19):

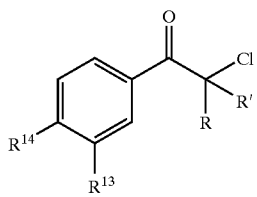
(19)

wherein $R^{14}$ represents a hydrogen or halogen atom, $R^{13}$ represents nitro, and both R and R' represent a hydrogen atom, said process comprising:
chlorinating a compound of the formula (18):

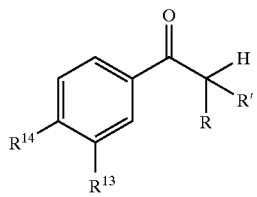
(18)

wherein $R^{13}$, $R^{14}$, R and R' are as defined above, with sulfuryl chloride in an ether solvent to give the compound of the formula (19).

In the present invention described in this chapter, the halogen atom represented by $R^{12}$ represents a fluorine, chlorine, bromine, or iodine atom, with fluorine, chlorine and bromine atoms being preferred. The "lower" in the lower alkyl group means a linear or branched saturated hydrocarbon having 1 to 4 carbon atoms and preferred examples thereof may include, for example, methyl, ethyl, n-propyl, i-propyl, n-butyl, i-butyl, s-butyl and t-butyl with methyl being preferred. The acyloxy may include acetyloxy, propionyloxy, isopropionyloxy, butyryloxy, benzoyloxy and the like with acetyloxy and benzoyloxy being preferred. The acylamino may include acetylamino, propionylamino, isopropionylamino, butyrylamino, benzoylamino and the like with acetylamino and benzoylamino being preferred. The aryl may include phenyl, 1-naphthyl, 2-naphthyl and the like and may optionally have any suitable substituent(s), such as, for example, a halogen atom and a lower alkyl group, at any suitable position(s) on the phenyl, 1-naphthyl and 2-naphthyl. A preferred example of the aryl may be phenyl.

R² represents an amino-protecting group and examples thereof include acetyl, benzyl, naphthyl and the like groups with benzyl group being preferred.

The acetophenone derivative of the formula (16) used in the present invention may include: acetophenone, 2'-chloroacetophenone, 3'-chloroacetophenone, 4'-chloroacetophenone, 2'-bromoacetophenone, 3'-bromoacetophenone, 4'-bromoacetophenone, 2'-nitroacetophenone, 3'-nitroacetophenone, 4'-nitroacetophenone, 2'-cyanoacetophenone, 3'-cyanoacetophenone, 4'-cyanoacetophenone, 2'-trifluoromethylacetophenone, 3'-trifluoromethylacetophenone, 4'-trifluoromethylacetophenone, 4'-chloro-3'-nitroacetophenone, 4'-bromo-3'-nitroacetophenone, 4'-acetyloxy-3'-nitroacetophenone, N-benzyl-N-(3-acetylphenyl)methanesulfonamide, N-benzyl-N-(5-acetyl-2-chlorophenyl)methanesulfonamide, N-benzyl-N-(5-acetyl-2-bromophenyl)methanesulfonamide, N-benzyl-N-(5-acetyl-2-acetyloxyphenyl)methanesulfonamide, N-(3-acetylphenyl)methanesulfonamide, N-(5-acetyl-2-chlorophenyl)methanesulfonamide, N-(5-acetyl-2-bromophenyl)methanesulfonamide, and N-(5-acetyl-2-acetyloxyphenyl)methanesulfonamide. These acetophenone derivatives are known and commercially available. Alternatively, they may be easily synthesized according to the method described in, for example, Larsen, et al., *J. Med. Chem.*, 10, p. 462 (1967) or C. Kaiser, et al., *J. Med. Chem.*, 7, p. 49 (1974). If necessary, those commercially available products or synthesized products may be subjected to known acylation or amino group-protection described in "Jikken Kagaku Koza (Course of Experimental Chemistry), 4th Ed." Vol. 22, published by Maruzen, Japan.

The resulting α-chloroacetophenone derivative of the formula (17) is also known and some of α-chloroacetophenone derivatives are commercially available. These α-chloroacetophenones are important intermediates in organic synthesis chemistry. They are used as intermediate materials for agricultural chemicals and are also important intermediates for synthesizing drugs, in particular β-adrenergic drugs as described in Jonathan, et al.,*J. Med. Chem.*, 35, p. 3081 (1992) and Chapter 1. Thus, they have great utilities.

The ether solvents used in the present invention are not particularly limited and include all solvents, so long as they have an ether linkage and may be used as solvents. Examples thereof include diethyl ether, di-n-propyl ether, diisopropyl ether, methyl t-butyl ether, tetrahydrofuran, tetrahydropyran, 1,3-dioxolane, 1,4-dioxane, 1,2-dimethoxyethane and the like. Among them, diisopropyl ether or methyl t-butyl ether is particularly preferred. These ether solvents may be used either alone or as any mixture thereof; however, a single solvent is preferably used. Any other solvent(s) may be added if convenient although it is generally preferable to use the ether solvent as a single solvent.

The amount of solvent used may be generally in the range of 1 to 50 ml, preferably 5 to 20 ml, per g of the acetophenone derivative of the formula (16). The amount of sulfuryl chloride used is 1 to 5 moles, preferably 1 to 3 moles, per mole of the acetophenone derivative; however, other ratios may be used if necessary.

This reaction may be carried out at a temperature in the range of from 0° C. to the reflux temperature of the exemplified solvent, preferably from room temperature to the reflux temperature of the exemplified solvent. The reaction time may be in the range of 0.1 to 72 hours. Since the reaction can be easily monitored by thin layer chromatography (TLC), high performance liquid chromatography (HPLC), or other analytical procedures, the reaction is preferably terminated at such a point that the yield of a desired α-chloroacetophenone reaches a maximum.

The α-chloroacetophenones, which are final products in the present invention, generally have lower solubilities than the starting acetophenones and, therefore, they may be precipitated in the reaction system as a solid depending upon the ether used. In these cases, the desired product may be obtained from the solution after the reaction through filtration and washing only and, therefore, these are preferable in view of simplicity of the operations. Even when they are not precipitated, the desired α-chloroacetophenones can be easily isolated by any usual purification methods conventionally used in chemical fields, such as distillation, recrystallization, and various column chromatographies.

EXAMPLES

The present invention will be further illustrated by way of the following examples, which do not limit the present invention in any way.

Thin layer chromatography (TLC) used Precoated silica gel 60 $F_{254}$ (Merck). After development with a solvent described in each Example, detection was effected by UV irradiation (254 nm) and coloration with ninhydrin. Rf values of TLC correspond to free amines. Organic solvents were dried over anhydrous magnesium or sodium sulfate. Column chromatography used silica gel (Wako-gel C-200: Wako Pure Chemical Industries).

Melting points (mp) were measured using BUCHI 510 (BUCHI).

Nuclear magnetic resonance spectra (NMR) were measured using AC-200P (FT-NMR, BRUKER). Chemical shifts using tetramethylsilane (TMS) as the internal standard are shown as δ (ppm), and coupling constants are shown as J (Hz). Mass spectra (MS) were measured by fast atom bombardment mass spectrometry (FAB-MS) using JEOL-JMS-SX102.

Reference Example

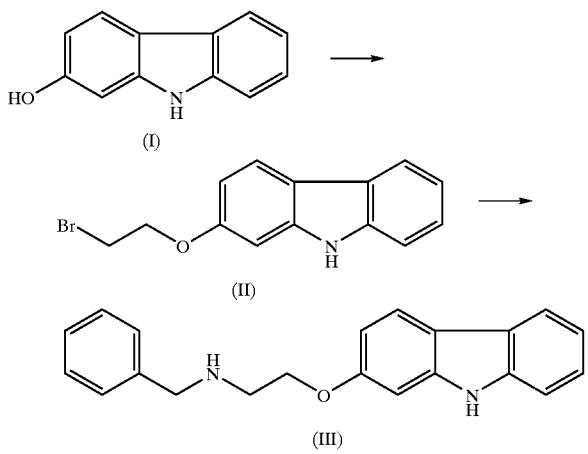

The compound (I) (30 g, Aldrich), potassium carbonate (113.1 g, Wako Pure Chemical Industries) and a mixture of 1,2-dibromoethane (211 ml, Wako Pure Chemical Industries) and 2-butanone (165 ml) were vigorously stirred at reflux temperature for 28 hours. The reaction mixture was poured into water (1050 ml) all at once. After stirring, crystals were filtered out, washed sequentially with water (1000 ml) and 2-propanol (250 ml), and dried under reduced pressure at room temperature to yield the compound (II) (43.43 g) as a white solid.

Rf=0.51 (ethyl acetate:n-hexane=1:2), $^1$H-NMR (DMSO-d$_6$): 3.82–3.85 (2H, m), 4.36–4.43 (2H, m), 6.80 (1H, dd, J=8.5, 2.2), 6.99 (1H, d, J=2.2), 7.11 (1H, m), 7.29 (1H, m), 7.42 (1H, d, J=8.3), 7.98 (1H, d, J=8.5), 8.00 (1H, d, J=7.7), 11.13 (1H, s)

HPLC: retention time (36.0 min) (column: COSMOSIL ODS-5 (GL Science; 4.6 mm ID×150 mm), solvent: 50 mM aqueous potassium dihydrogenphosphate solution/methanol=4/6, flow rate: 1.0 ml/min, detection wave length: 254 nm, 25° C.)

Then, said compound (II) (32 g) was mixed with benzylamine (111 ml, Wako Pure Chemical Industries) and stirred for 20 minutes under heating at the internal temperature of 95° C. The reaction mixture was poured into water (930 ml) all at once and stirred for 30 minutes. Then, crystals were filtered out, washed with water (600 ml) and 2-propanol (400 ml), and dried under reduced pressure at room temperature to yield a white-yellow solid (34.9 g). This solid was purified by column chromatography using silica gel (1.5 Kg) (eluent: n-hexane:ethyl acetate=3:2 and ethyl acetate:ethanol=4:1) to yield the compound (III) (30.7 g) as a white-yellow compound.

Melting point: 167–169° C.

Rf=0.33 (ethyl acetate:n-hexane=1:2),

Mass: 317 (MH$^+$)

$^1$H-NMR (DMSO-d$_6$): 2.30 (1H, s), 2.91 (2H, t, J=5.8), 3.79 (2H, s), 4.11 (2H, t, J=5.8), 6.77 (1H, dd, J=8.5, 2.2), 6.96 (1H, d, J=2.2), 7.10 (1H, m), 7.20–7.44 (7H, m), 7.92–8.00 (2H, m), 11.09 (1H, s)

HPLC: retention time (8.0 min) (column: COSMOSIL ODS-5 (GL Science; 4.6 mm ID×150 mm), solvent: 50 mM aqueous potassium dihydrogenphosphate solution/methanol=4/6, flow rate: 1.0 ml/min, detection wave length: 254 nm, 25° C.)

EXAMPLE 1

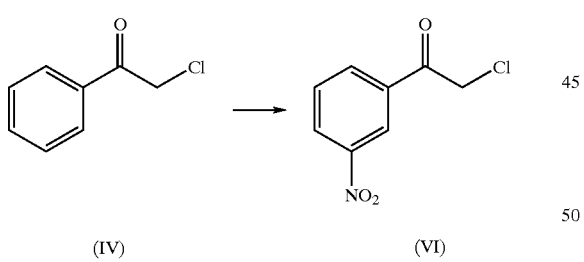

The compound (VI) was synthesized from the compound (IV) according to the method reported by H. G. Garg, et al. in *J. Chem. Soc. C*, 4, p. 607 (1969). Thus, the compound (IV) (1.0 g, TOKYO KASEI KOGYO) was portionwise added to ice-cooled fuming nitric acid (10 ml, Wako Pure Chemical Industries) so that the temperature of the reaction mixture did not exceed 5° C. After stirring for 1 hour under ice-cooling, the reaction mixture was added into ice-water (100 ml). The precipitate was twice extracted with ethyl acetate (50 ml), and combined organic layers were washed with aqueous saturated sodium chloride solution (50 ml). After the organic layer was dried, the solvent was distilled off under reduced pressure and the residue was washed with diethyl ether to yield the compound (VI).

Melting point: 98–100° C.,

Rf=0.55 (ethyl acetate:n-hexane=1:2), $^1$H-NMR (DMSO-d$_6$): 5.33 (2H, s), 7.83–7.91 (1H, m), 8.37–8.41 (1H, m), 8.48–8.54 (1H, m), 8.68 (1H, brs)

HPLC: retention time (8.4 min) (column: COSMOSIL ODS-5 (GL Science; 4.6 mm ID×150 mm), solvent: 50 mM aqueous potassium dihydrogenphosphate solution/acetonitrile=6/4, flow rate: 1.0 ml/min, detection wave length: 254 nm, 25° C.)

EXAMPLE 2

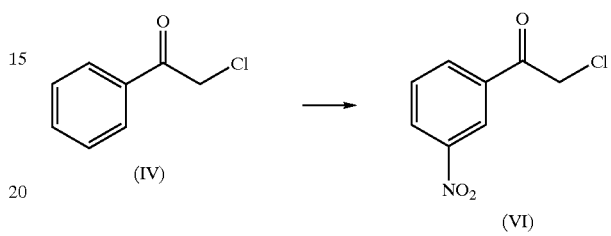

The compound (VI) was synthesized from the compound (IV) using the alternative method reported by Charles Barkenbus, et al. in *J. Am. Chem. Soc.*, 56, pp. 1369–1370 (1934). Thus, the compound (IV) (1.0 g, TOKYO KASEI KOGYO) was portionwise added to concentrated sulfuric acid (9.4 ml, KOKUSAN CHEMICAL) cooled to −20° C. or below. After the compound (IV) was dissolved, a mixture of concentrated sulfuric acid (0.8 ml) and nitric acid (0.6 ml, Wako Pure Chemical Industries) was added while the temperature of the reaction mixture was held at −20° C. or below. After stirring for 30 minutes at that temperature, the reaction mixture was added to ice (20 g), and water (50 ml) was added. The precipitate was twice extracted with ethyl acetate (50 ml), and combined organic layers were washed with aqueous saturated sodium chloride solution (50 ml). After drying the organic layer, the solvent was distilled off under reduced pressure and the residue was washed with diethyl ether to yield the compound (VI).

The thus obtained compound had the same properties in TLC and HPLC as the compound obtained in Example 1.

EXAMPLE 3

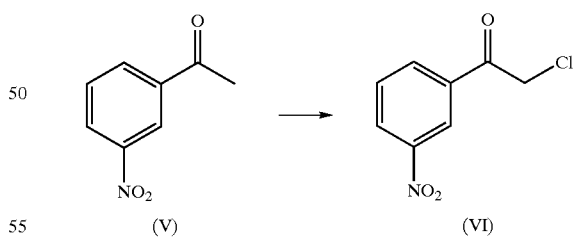

The compound (VI) was synthesized from the compound (V) according to the method reported by Hak Jin Kim, et al. in *Bull. Korea Chem. Soc.*, 11, pp. 184–186 (1990). Thus, the compound (V) (1.0 g, TOKYO KASEI KOGYO) was dissolved in dimethylformamide (20 ml) and a mixture of concentrated hydrochloric acid (1.5 ml, KATAYAMA CHEMICAL) and dimethylformamide (16.5 ml). Then, m-chloroperbenzoic acid (3.0 g, TOKYO KASEI KOGYO, about 70% content) was added and stirred at room temperature for 6 hours. The reaction mixture was added to ice-cooled 5% aqueous potassium carbonate solution (250 ml) and extracted twice with diethyl ether (160 ml). The organic layers were combined and washed twice with 5% aqueous potassium carbonate solution (125 ml). The organic layer was dried and the solvent was distilled off under reduced pressure. The residue was purified by column chromatography using silica gel (25 g) (eluent: n-hexane:ethyl acetate= 2:1) to yield the compound (VI) as a white crystal.

The thus obtained compound had the same properties in TLC and HPLC as the compound obtained in Example 1.

EXAMPLE 4

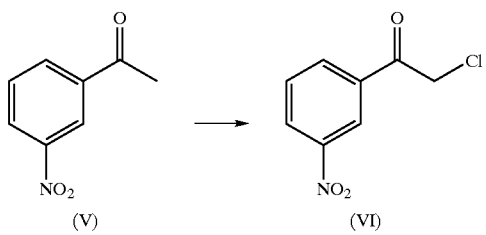

To a solution of the compound (V) (1.5 g, TOKYO KASEI KOGYO) in dichloromethane (9 ml) and methanol (1.5 ml), a solution of sulfuryl chloride (2.0 g, Wako Pure Chemical Industries) in dichloromethane (2 ml) was dropwise added at room temperature over 1 hour. After completion of the reaction, water (5 ml) was added and stirred at room temperature for 1 hour, and the organic layer was separated. The solvent was distilled off under reduced pressure to yield a yellow crystal as a residue. Then, this residue was dissolved in dichloromethane (10 ml), washed with 0.1N aqueous sodium hydroxide solution (5 ml) and dried. The solvent was distilled off under reduced pressure to yield a yellow crystal as a residue. Diethyl ether (5 ml) was added to this residue. After the suspension was stirred at room temperature, the residue was filtered and dried under reduced pressure at room temperature to yield the compound (VI) as a white crystal.

The thus obtained compound had the same properties in TLC and HPLC as the compound obtained in Example 1.

EXAMPLE 5

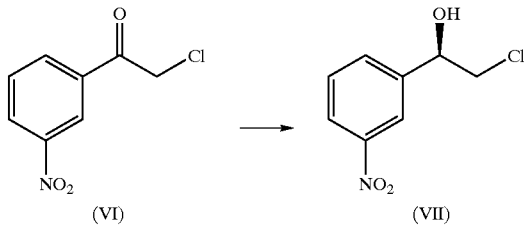

The compound (VI) (80 g) obtained in Example 1 was dissolved in 2-propanol (700 ml), and [(S,S)-N-methanesulfonyl-1,2-diphenylethylenediamine](p-cymene) ruthenium complex (768 mg) synthesized according to the method reported by Noyori, et al. in *J. Am. Chem. Soc.*, 118, p. 2521 (1996) was added. Then, formic acid/triethylamine mixture [formic acid/triethylamine complex 5:2, FLUKA] (100 ml) was added and stirred at room temperature for 22 hours.

After the reaction, ethyl acetate (2000 ml) was added to the reaction mixture and washed sequentially with water (400 ml), 1N hydrochloric acid (400 ml), 1N aqueous sodium hydroxide solution (400 ml) and water (400 ml). The organic layer was dried and the solvent was distilled off under reduced pressure to yield the compound (VII) (76.8 g) as a pale yellow oil.

Rf=0.55 (ethyl acetate:n-hexane=1:2), $^1$H-NMR (DMSO-$d_6$): 3.80 (1H, dd, J=8.3, 4.5), 3.88 (1H, dd, J=8.4, 3.3), 5.04 (1H, m), 6.15 (1H, d, J=3.3), 7.67 (1H, m), 7.92 (1H, m), 8.17 (1H, m), 8.32 (1H, brs)

HPLC: retention time (5.4 min) (column: COSMOSIL ODS-5 (GL Science; 4.6 mm ID×150 mm), solvent: 50 mM aqueous potassium dihydrogenphosphate solution/ acetonitrile=6/4, flow rate: 1.0 ml/min, detection wave length: 254 nm, 25° C.)

HPLC: retention time (R-form: 19.8, min) (column: CHIRALPAK AS (DAICEL CHEMICAL INDUSTRIES; 4.6 mm ID×250 mm), solvent: n-hexane/ethanol=9/1, flow rate: 0.5 ml/min, detection wave length: 254 nm, 25° C.). The retention time of S-form was 21.5 minutes.

EXAMPLE 6

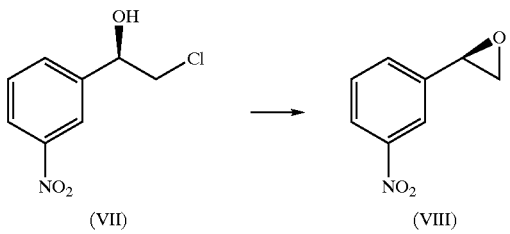

The compound (VII) (76.8 g) obtained in Example 5 was dissolved in 2-propanol (2000 ml) and 2N aqueous sodium hydroxide solution (300 ml) was added over 20 minutes. After stirring at room temperature for 30 minutes, the reaction mixture was cooled with ice and ice-cooled water (7500 ml) was added over 1 hour under stirring. Under ice cooling, the mixture was stirred for 30 minutes and the precipitated crystal was filtered and dried under reduced pressure at room temperature to yield the compound (VIII) (52.5 g) as a pale yellow crystal.

Melting point: 38–39° C.,

Rf=0.60 (ethyl acetate:n-hexane=1:2), $^1$H-NMR (DMSO-$d_6$): 2.93 (1H, dd, J=5.3, 2.5), 3.22 (1H, dd, J=5.2, 4.1), 4.15 (1H, dd, J=4.1, 2.6), 7.64–7.79 (2H, m), 8.11–8.21 (2H, m)

HPLC: retention time (6.9 min) (column: COSMOSIL ODS-5 (GL Science; 4.6 mm ID×150 mm), solvent: 50 mM aqueous potassium dihydrogenphosphate solution/ acetonitrile=6/4, flow rate: 1.0 ml/min, detection wave length: 254 nm, 25° C.)

HPLC: retention time (R-form: 16.1 min) (column: CHIRALPAK AD (DAICEL CHEMICAL INDUSTRIES; 4.6 mm ID×250 mm), solvent: n-hexane/ethanol=85/15, flow rate: 0.5 ml/min, detection wave length: 254 nm, 35° C.). The retention time of S-form was 13.8 minutes.

EXAMPLE 7

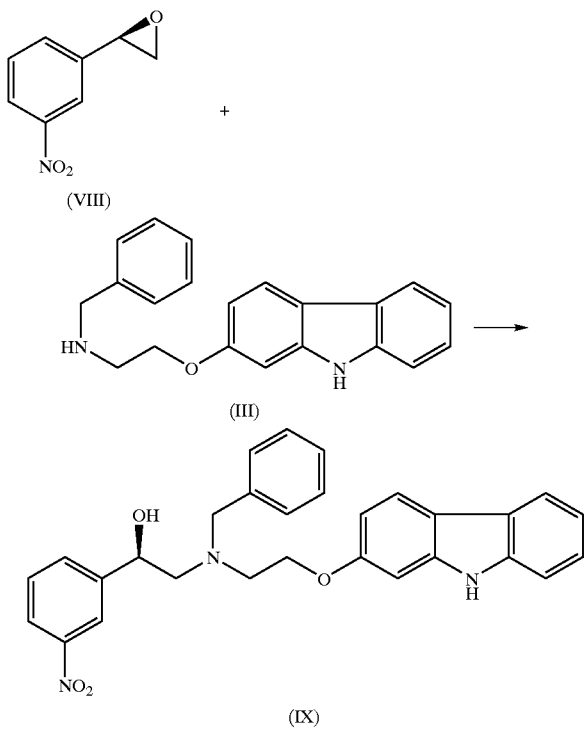

A mixture of the compound (VIII) (3.2 g) obtained in Example 6, the compound (III) (12.3 g) obtained in Reference Example and 2-butanol (96 ml) was stirred for 8 hours under heating at the internal temperature of 95° C. After cooling, the solvent was distilled off under reduced pressure. To the resulting residue, ethyl acetate (320 ml) and 0.5N hydrogen chloride/2-propanol solution (77.5 ml) were added and stirred at 0° C. for 1 hour. Insoluble materials were filtered out and aqueous saturated sodium chloride solution (320 ml) was added to the filtrate. The organic layer was separated, washed with aqueous saturated sodium bicarbonate (320 ml) and dried, and the solvent was distilled out under reduced pressure to yield the compound (IX) (8.35 g) as a pale yellow amorphous solid.

Rf=0.69 (ethyl acetate:n-hexane=1:1), $^1$H-NMR (DMSO-$d_6$): 2.79 (2H, t, J=6.4), 2.95 (2H, t, J=5.6), 3.71 (1H, d, J=13.9), 3.84 (1H, d, J=13.8), 4.01–4.08 (2H, m), 4.86 (2H, brs), 5.47 (1H, d, J=4.0), 6.70 (1H, dd, J=8.5, 2.2), 6.89 (1H, d, J=2.1), 7.06–7.59 (5H, m), 7.77–8.17 (4H, m), 11.06 (1H, s)

HPLC: retention time (7.8 min) (column: COSMOSIL 5C18-AR (nacalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

HPLC: retention time (R-form: 71.3 min) (column: CHIRALCEL OJ-R (DAICEL CHEMICAL INDUSTRIES; 4.6 mm ID×150 mm), solvent: 0.5 M aqueous sodium perchlorate solution (adjusted to pH 2 with perchloric acid)/acetonitrile=6/4, flow rate: 0.5 ml/min, detection wave length: 233 nm, 35° C.). The retention time of S-form was 65.0 minutes.

EXAMPLE 8

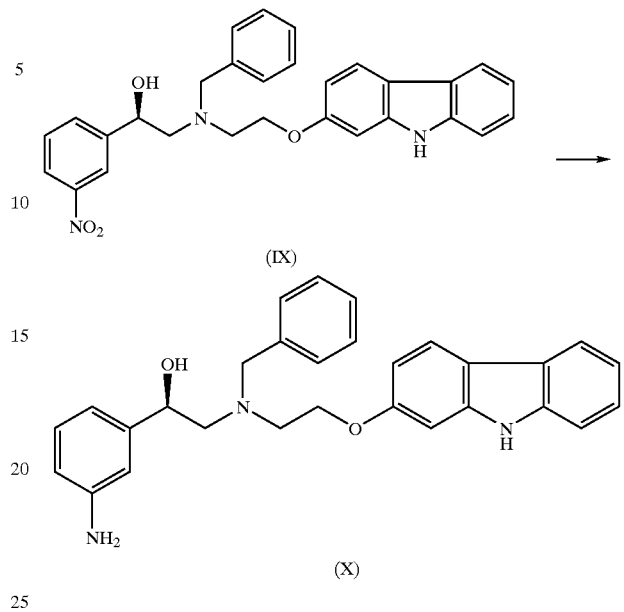

Platinum oxide (39 mg, Aldrich) was added to a solution of the compound (IX) (8.35 g) obtained in Example 7 in methanol (125 ml) and stirred for 4 hours under a hydrogen atmosphere at atmospheric pressure at room temperature. The catalyst was filtered out and the filtrate was distilled under reduced pressure to remove the solvent. Thus, the compound (X) (7.74 g) was obtained as a pale yellow amorphous solid.

Rf=0.36 (ethyl acetate:n-hexane=1:1), $^1$H-NMR (DMSO-$d_6$): 2.69 (2H, d, J=6.1), 2.97 (2H, brs), 3.83 (2H, brs), 4.05–4.08 (2H, m), 4.57 (2H, brs), 4.81 (1H, d, J=3.1), 4.94 (2H, brs), 6.40–6.47 (1H, m), 6.57 (1H, brs), 6.73 (1H, dd, J=8.6, 2.1), 6.89–6.96 (2H, m), 7.06–7.43 (4H, m), 7.92–7.99 (2H, m), 11.06 (1H, s)

HPLC: retention time (3.4 min) (column: COSMOSIL 5C18-AR (nacalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

HPLC: retention time (R-form: 10.4 min) (column: CHIRALCEL OJ-R (DAICEL CHEMICAL INDUSTRIES; 4.6 mm ID×150 mm), solvent: 0.5 M aqueous sodium perchlorate solution (adjusted to pH 2 with perchloric acid)/acetonitrile=6/4, flow rate: 0.5 ml/min, detection wave length: 233 nm, 35° C.). The retention time of S-form was 12.5 minutes.

EXAMPLE 9

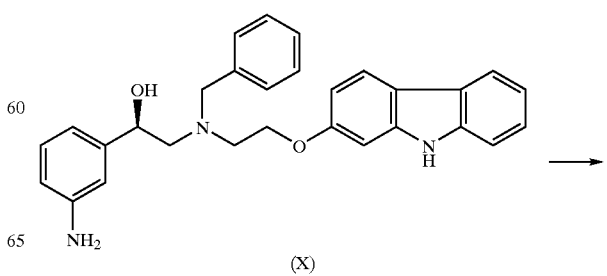

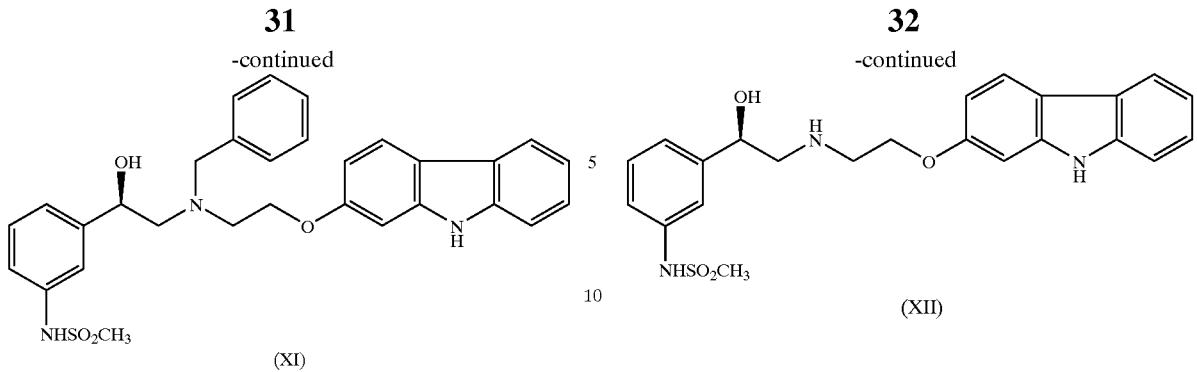

(XI)

Pyridine (11 ml, Wako Pure Chemical Industries) was added to a solution of the compound (X) (7.74 g) obtained in Example 8 in tetrahydrofuran (78 ml), and cooled to 0° C. Then, methanesulfonyl chloride (1.59 ml, TOKYO KASEI KOGYO) was added over 15 minutes and stirred at 0° C. for 4 hours. Ethyl acetate (200 ml) and 1N hydrochloric acid (200 ml) were added to the reaction mixture and the organic layer was separated. The resulting organic layer was washed sequentially with water (200 ml, twice), aqueous saturated sodium bicarbonate (200 ml), and aqueous saturated sodium chloride (200 ml) and dried. The solvent was distilled off under reduced pressure to yield the compound (XI) (9.0 g) as a light orange amorphous solid.

Rf=0.40 (methyl ethyl ketone: toluene=1:2), $^1$H-NMR (DMSO-d$_6$): 2.75 (2H, d, J=6.1), 2.91 (3H, s), 2.95–3.01 (2H, m), 3.80 (2H, brs), 4.02–4.09 (2H, m), 4.66–4.69 (2H, m), 5.47 (1H, brs), 6.73 (1H, dd, J=8.4, 1.9), 6.92 (1H, d, J=2.0), 7.02–7.45 (7H, m), 7.93–8.00 (2H, m), 11.06 (1H, s)

HPLC: retention time (3.1 min) (column: COSMOSIL 5C18-AR (nacalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

HPLC: retention time (R-form: 21.7 min) (column: CHIRALCEL OJ-R (DAICEL CHEMICAL INDUSTRIES; 4.6 mm ID×150 mm), solvent: 0.5 M aqueous sodium perchlorate solution (adjusted to pH 2 with perchloric acid)/acetonitrile=6/4, flow rate: 0.5 ml/min, detection wave length: 233 nm, 35° C.). The retention time of S-form was 27.7 minutes.

EXAMPLE 10

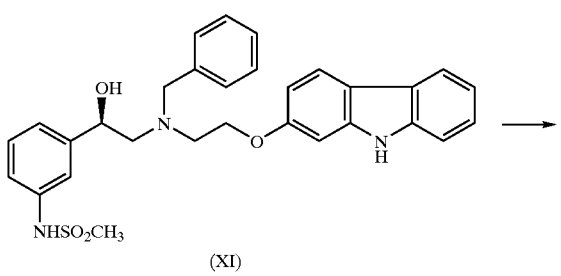

(XI)

(XII)

To a solution of the compound (XI) (2.0 g) obtained in Example 9 in ethanol (100 ml), 10% palladium-carbon (100 mg, Merck) was added, and stirred for 4 hours under a hydrogen atmosphere at atmospheric pressure at the internal temperature of about 70° C. After cooling, tetrahydrofuran (40 ml) was added and stirred for 30 minutes at room temperature. After filtration, the residue was washed with tetrahydrofuran (8 ml). The filtrate and the washing solution were combined and the solvent was distilled off under reduced pressure to yield the compound (XII) (1.2 g) as a pale yellow solid.

The thus obtained compound had the same retention time in HPLC as the compound obtained according to the known method (JP-A-9-249623), indicating that both compounds were identical with each other.

HPLC: retention time (6.6 min) (column: YMC-Pack Pro C18 (YMC; 4.6 mm ID×150 mm), solvent: 20 mM sodium phosphate buffer (pH 2.9)/acetonitrile=70/30, flow rate: 1.0 ml/min, detection wave length: 254 nm, 25° C.)

HPLC: retention time (R-form: 24.6 min) (column: CHIRALCEL OJ-R (DAICEL CHEMICAL INDUSTRIES; 4.6 mm ID×150 mm), solvent: 0.5 M aqueous sodium perchlorate solution (adjusted to pH 2 with perchloric acid)/acetonitrile=6/4, flow rate: 0.5 ml/min, detection wave length: 233 nm, 35° C.). The retention time of S-form was 22.1 minutes.

EXAMPLE 11

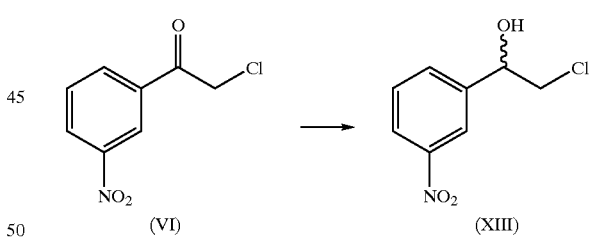

(VI)

(XIII)

Methanol (250 ml) and tetrahydrofuran (50 ml) were added to dissolve the compound (VI) (5.0 g) synthesized in Example 1, and cooled with ice. Then, sodium borohydride (480 mg, KATAYAMA CHEMICAL) was added and stirred at room temperature for 2 hours. 1N hydrochloric acid (13 ml) was added and the solvent was distilled off under reduced pressure. To the residue, ethyl acetate (300 ml) and water (300 ml) were added. The organic layer was separated and dried and the solvent was distilled off under reduced pressure to yield the compound (XIII) (5.0 g).

The thus obtained compound had the same properties in TLC and HPLC as the compound obtained in Example 5.

Rf=0.55 (ethyl acetate:n-hexane=1:2),

HPLC: retention time (5.4 min) (column: COSMOSIL ODS-5 (GL Science; 4.6 mm ID×150 mm), solvent: 50 mM

EXAMPLE 12

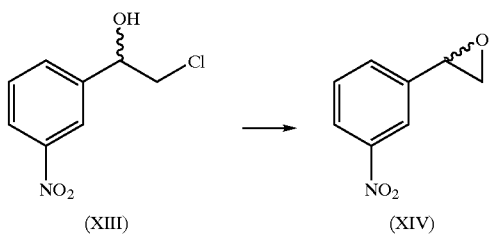

To a solution of the compound (XIII) (5.0 g) obtained in Example 11 in methanol (80 ml), 1N aqueous sodium hydroxide solution (40 ml) was added over 10 minutes. After stirring at room temperature for 30 minutes, ethyl acetate (300 ml) and water (300 ml) were added to the reaction mixture and the organic layer was separated. The organic layer was dried and the solvent was distilled off under reduced pressure to yield the compound. (XIV) (3.9 g) as a pale yellow oil.

The thus obtained compound had the same properties in TLC and HPLC as the compound obtained in Example 6.

Rf=0.60 (ethyl acetate:n-hexane=1:2),

HPLC: retention time (6.9 min) (column: COSMOSIL ODS-5 (GL Science; 4.6 mm ID×150 mm), solvent: 50 mM aqueous potassium dihydrogenphosphate solution/acetonitrile=6/4, flow rate: 1.0 ml/min, detection wave length: 254 nm, 25° C.)

EXAMPLE 13

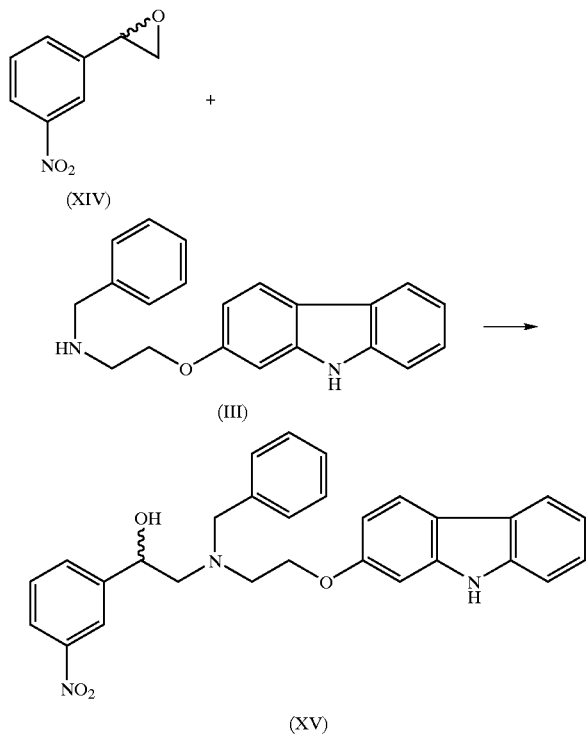

A mixture of the compound (XIV) (1.6 g) obtained in Example 12, the a compound (III) (6.3 g) obtained in Reference Example and 2-butanol (48 ml) was stirred for 8 hours under heating at the internal temperature of 95° C. After cooling, the solvent was distilled off under reduced pressure and ethyl acetate (160 ml) and 0.5N hydrogen chloride/2-propanol solution (39 ml) were added to the resulting residue followed by stirring at 0° C. for 1 hour. Insoluble materials were filtered out and the compound (III) was recovered in the form of hydrochloride. Then, aqueous saturated sodium chloride (160 ml) was added to the filtrate and the organic layer was separated. This organic layer was washed with aqueous saturated sodium bicarbonate (160 ml) and dried. Then, the solvent was distilled off under reduced pressure to yield the compound (XV) (4.2 g) as a pale yellow amorphous solid.

The thus obtained compound had the same properties in TLC and HPLC as the compound obtained in Example 7.

Rf=0.69 (ethyl acetate:n-hexane=1:1),

HPLC: retention time (7.8 min) (column: COSMOSIL 5C18-AR (nacalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

EXAMPLE 14

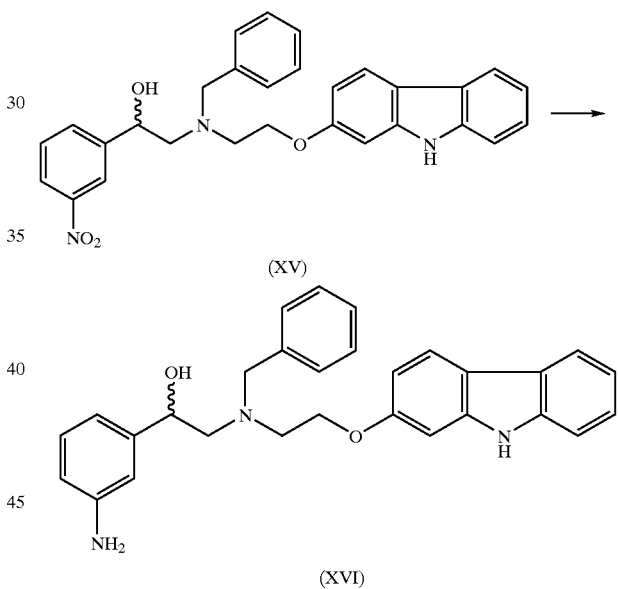

To a solution of the compound (XV) (4.8 g) obtained in Example 13 in methanol (72 ml), platinum oxide (24 mg, Aldrich) was added and stirred under a hydrogen atmosphere at atmospheric pressure at room temperature for 4 hours. The catalyst was filtered out and the solvent was distilled off under reduced pressure from the filtrate to yield the compound (XVI) (4.5 g) as a pale yellow amorphous solid.

The thus obtained compound had the same properties in TLC and HPLC as the compound obtained in Example 8.

Rf=0.36 (ethyl acetate:n-hexane=1:1),

HPLC: retention time (3.4 min) (column: COSMOSIL 5C18-AR (nacalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

EXAMPLE 15

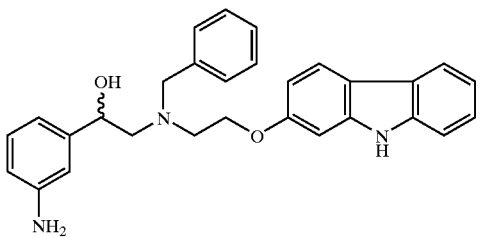

(XVI)

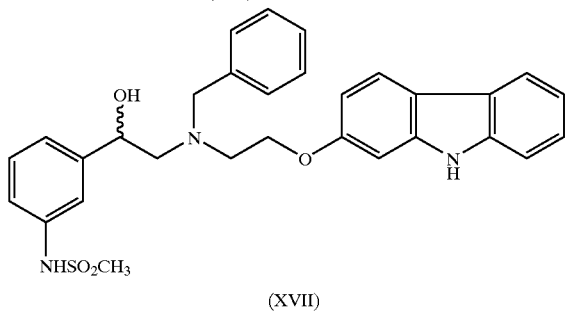

(XVII)

To a solution of the compound (XVI) (9.0 g) obtained in Example 14 in tetrahydrofuran (90 ml), pyridine (14 ml, Wako Pure Chemical Industries) was added and cooled to 0° C. Then, methanesulfonyl chloride (1.8 ml, Wako Pure Chemical Industries) was added over 15 minutes and stirred at 0° C. for 4 hours. Ethyl acetate (230 ml) and 1N hydrochloric acid (230 ml) were added to the reaction mixture and the organic layer was separated. The organic layer was washed sequentially with water (230 ml, twice), aqueous saturated sodium bicarbonate (230 ml), and aqueous saturated sodium chloride (230 ml). After drying, the solvent was distilled off under reduced pressure to yield the compound (XVII) (10.5 g) as a light orange amorphous solid.

The thus obtained compound had the same properties in TLC and HPLC as the compound obtained in Example 9.

Rf=0.40 (methyl ethyl ketone:toluene=1:2),

HPLC: retention time (3.1 min) (column: COSMOSIL 5C18-AR (nakalai tesque; 6.0 mm ID×150 mm), solvent: 5 mM aqueous potassium dihydrogenphosphate solution/methanol=2/8, flow rate: 1.0 ml/min, detection wave length: 254 nm, 25° C.)

EXAMPLE 16

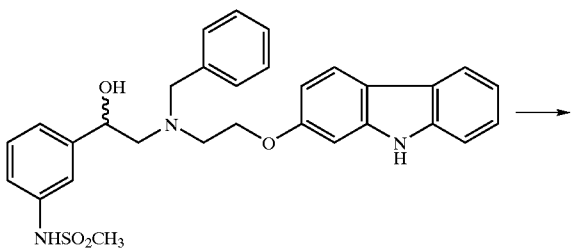

(XVII)

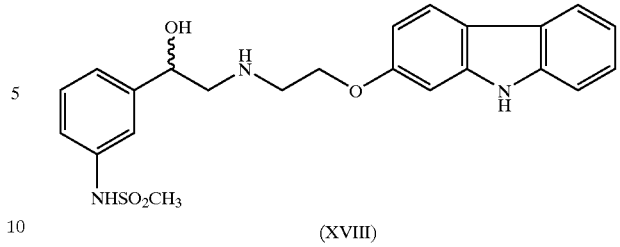

(XVIII)

To a solution of the compound (XVII) (2.5 g) obtained in Example 15 in ethanol (130 ml), 10% palladium-carbon (125 mg, Merck) was added and stirred for 4 hours under a hydrogen atmosphere at atmospheric pressure at the internal temperature of about 70° C. After cooling, tetrahydrofuran (50 ml) was added and stirred at room temperature for 30 minutes followed by filtration. The residue was washed with tetrahydrofuran (10 ml) and the filtrate and the washing solution were combined. The solvent was distilled off under reduced pressure to yield the compound (XVIII) (1.5 g) as a pale yellow solid.

The thus obtained compound had the same properties in HPLC as the compound obtained in Example 10.

HPLC: retention time (6.6 min) (column: YMC-Pack Pro C18 (YMC; 4.6 mm ID×150 mm), solvent: 20 mM sodium phosphate buffer (pH 2.9)/acetonitrile=70/30, flow rate: 1.0 ml/min, detection wave length: 254 nm, 25° C.)

EXAMPLE 17

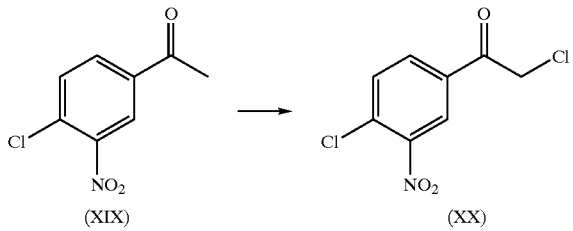

(XIX)      (XX)

To a solution of the compound (XIX) (60.7 g, Lancaster) in dichloromethane (300 ml) and methanol (24.4 ml), a solution of sulfuryl chloride (81.8 g, Wako Pure Chemical Industries) in dichloromethane (120 ml) was dropwise added under ice-cooling over 40 minutes. After completion of the reaction, water (215 ml) was added and the organic layer was separated. The organic layer was washed with water and dried, and the solvent was distilled off under reduced pressure to yield a yellow solid as a residue. This solid was pulverized in a mortar and dispersed and stirred in diisopropyl ether (60 ml) for 30 minutes. After filtration, the residue was further washed with diisopropyl ether (40 ml) and dried under reduced pressure to yield the compound (XX) as a yellow solid.

Rf=0.50 (ethyl acetate:n-hexane=1:2), $^1$H-NMR (CDCl$_3$): 4.65 (2H, s), 7.73 (1H, d, J=8.6), 8.11 (1H, dd, J=8.3, 2.0), 8.45 (1H, d, J=2.0)

HPLC: retention time (5.6 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 30° C.)

EXAMPLE 18

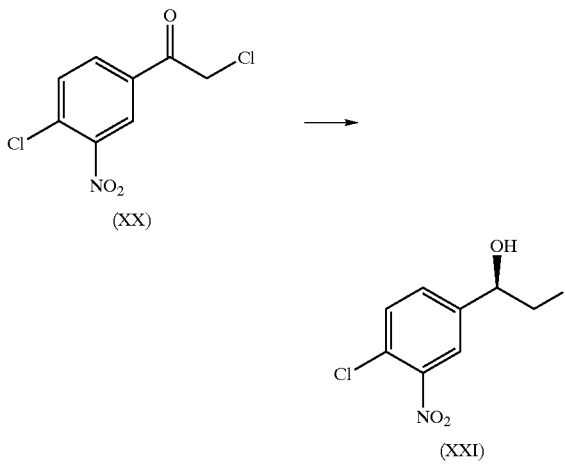

The compound (XX) (234 mg) synthesized in Example 17 was dissolved in tetrahydrofuran (0.5 ml), and [(S,S)-N-methanesulfonyl-1,2-diphenylethylenediamine](p-cymene) ruthenium complex (5.6 mg) synthesized according to the method reported by Noyori, et al. in *J. Am. Chem. Soc.*, 118, p. 2521 (1996) was added. Then, a mixture of formic acid/triethylamine [formic acid/triethylamine complex 5:2, FLUKA] (0.5 ml) was added and stirred at room temperature for 19.5 hours.

After completion of the reaction, ethyl acetate (6 ml) and water (2 ml) were added to the reaction mixture and vigorously stirred. The separated organic layer was washed three times with 1.2N hydrochloric acid (2 ml) and then with aqueous saturated sodium chloride (2 ml) and dried. After distilling off the solvent under reduced pressure, the residue was purified by silica gel chromatography (eluent; ethyl acetate:n-hexane=1:4) and concentrated to yield the compound (XXI) (153 mg).

Rf=0.35 (ethyl acetate:n-hexane=1:2), $^1$H-NMR (CDCl$_3$): 2.82 (1H, d, J=3.6), 3.65 (1H, dd, J=11.6, 3.6), 3.75 (1H, dd, J=11.2, 7.9), 4.99 (1H, ddd, J=11.6, 7.9, 3.6), 7.57 (2H, s), 7.95 (1H, s)

HPLC: retention time (4.9 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30 to (5 min) 10/90, and then held at 10/90, flow rate: 1.0 ml/min, detection wave length: 233 nm, 30° C.)

HPLC: retention time (R-form: 20.3 min) (column: CHIRALPAK AS (DAICEL CHEMICAL INDUSTRIES; 4.6 mm ID×250 mm), solvent: n-hexane/ethanol=90/10, flow rate: 0.5 ml/min, detection wave length: 254 nm, 40° C.). The retention time of S-form was 17.6 minutes.

EXAMPLE 19

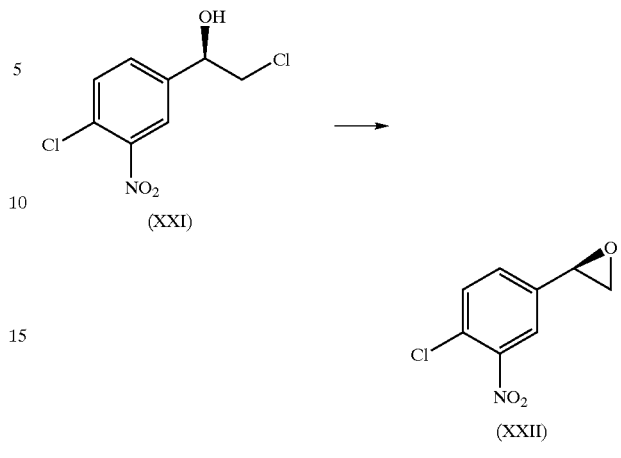

To a solution of the compound (XXI) (153 mg) obtained in Example 18 in 2-propanol (2.6 ml), 1N aqueous sodium hydroxide solution (1.48 ml) was added. After stirring at room temperature for 30 minutes, ice water (2.6 ml) was added. The precipitated white solid was filtered and dried under reduced pressure to yield the compound (XXII) (60.9 mg).

Rf=0.50 (ethyl acetate:n-hexane=1:2), $^1$H-NMR (CDCl$_3$): 2.76 (1H, dd, J=2.3, 2.6), 3.21 (1H, dd, J=5.3, 4.0), 3.92 (1H, dd, J=4.0, 2.3), 7.44 (1H, dd, J=8.3, 2.0), 7.54 (1H, d, J=8.2), 7.80 (1H, d, J=2.0)

HPLC: retention time (5.2 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 30° C.)

HPLC: retention time (R-form: 13.1 min) (column: CHIRALPAK AD (DAICEL CHEMICAL INDUSTRIES; 4.6 mm ID×250 mm), solvent: n-hexane/ethanol=90/10, flow rate: 0.5 ml/min, detection wave length: 254 nm, 40° C.). The retention time of S-form was 14.2 minutes.

EXAMPLE 20

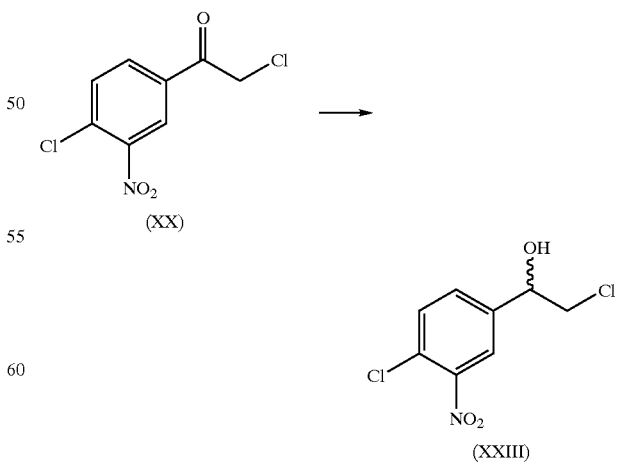

Methanol (5 ml) and 1,4-dioxane (10 ml) were added to dissolve the compound (XX) (697 mg) synthesized in Example 17 and cooled with ice. Then, sodium borohydride (42 mg, nacalai tesque) was added and stirred at the external temperature of 2° C. for 20 minutes. Then, 1N hydrochloric acid (34 ml) was portionwise added, and further ethyl acetate (67 ml) was added followed by separating an organic layer. The organic layer was washed with aqueous saturated sodium bicarbonate (34 ml) and aqueous saturated sodium chloride (34 ml) and dried. The solvent was distilled off under reduced pressure to yield the compound (XXIII) as a yellow oil.

The thus obtained compound had the same properties in TLC and HPLC as the compound obtained in Example 18.

Rf=0.35 (ethyl acetate:n-hexane=1:2),

HPLC: retention time (4.9 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 30° C.)

EXAMPLE 21

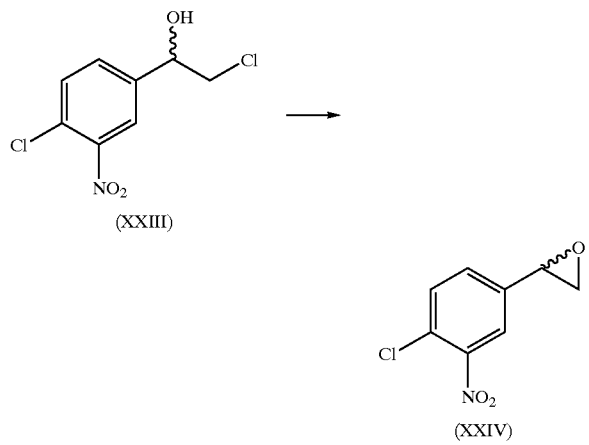

To a solution of the compound (XXIII) (668 mg) obtained in Example 20 in methanol (10 ml), 1N aqueous sodium hydroxide solution (3 ml) was added and stirred at room temperature for 2 hours. Then, ethyl acetate (40 ml) and aqueous saturated sodium chloride (20 ml) were added and the separated organic layer was washed with aqueous saturated sodium chloride (20 ml). After drying, the solvent was distilled off under reduced pressure and the residue was purified by silica gel chromatography (eluent; ethyl acetate:n-hexane=1:9) to yield the compound (XXIV) as pale yellow oil.

The thus obtained compound had the same properties in TLC and HPLC as the compound obtained in Example 19.

Rf=0.50 (ethyl acetate:n-hexane=1:2),

HPLC: retention time (5.2 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 30° C.)

EXAMPLE 22

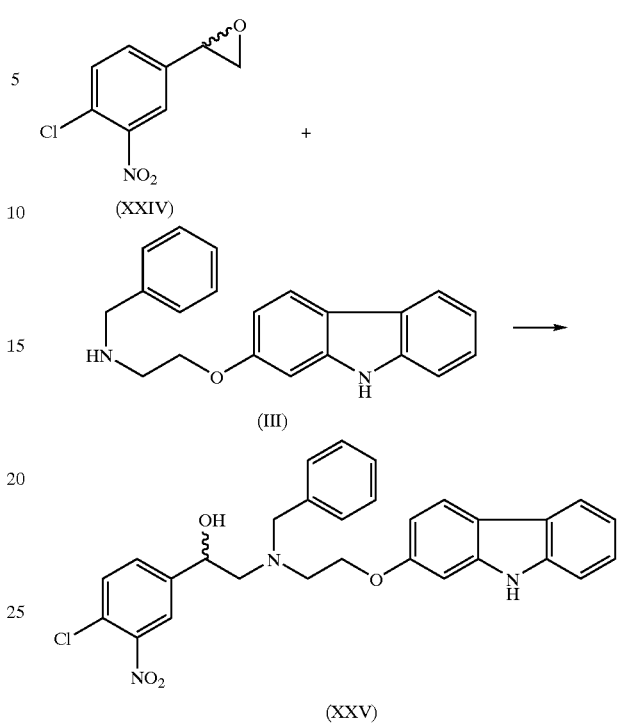

A mixture of the compound (XXIV) (11.7 g) obtained in Example 21, the compound (III) (20.0 g) obtained in Reference Example and 2-butanol (120 ml) was stirred for 20 hours while heating at the external temperature of 110° C. After cooling, the solvent was distilled off under reduced pressure, and acetonitrile (120 ml) and active carbon (Shirasagi A, Takeda Chemical Industries) (12.4 g) were added to the resulting residue and stirred at room temperature for 30 minutes. Insoluble materials were filtered out and the solvent was distilled off under reduced pressure. The residue was purified by silica gel chromatography (eluent; chloroform) and concentrated to yield the compound (XXV) (22.3 g) as a pale yellow amorphous solid.

Rf=0.62 (ethyl acetate:n-hexane=1:1), $^1$H-NMR (DMSO-d$_6$): 2.80 (1H, dd, J=13.2, 6.9), 2.90 (1H, dd, J=13.2, 5.9), 3.04 (2H, t, J=5.6), 3.76 (1H, d, J=13.9), 3.91 (1H, d, J=13.9), 4.14 (2H, t, J=5.6), 4.87–4.90 (1H, m), 6.79 (1H, dd, J=8.6, 2.3), 6.99 (1H, d, J=2.0), 7.16–7.22 (1H, m), 7.28 (5H, brs), 7.33–7.39 (1H, m), 7.50 (1H, d, J=7.9), 7.68–7.75 (2H, m), 8.02–8.08 (3H, m)

HPLC: retention time (6.6 min) (column: WAKOSIL-II 3C18HG (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 30° C.)

EXAMPLE 23

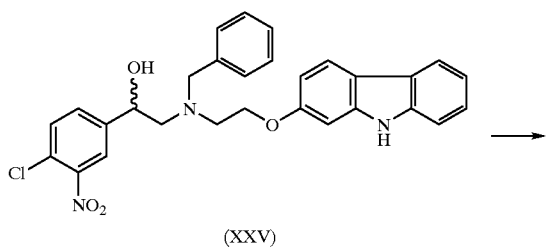

(XXV)

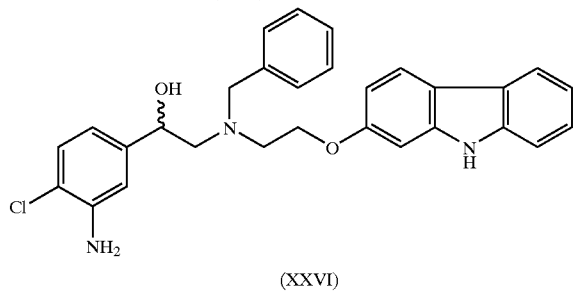

(XXVI)

To a solution of the compound (XXV) (4.5 g) obtained in Example 22 in ethanol (70 ml), bis(2,4-pentanedionato) copper (234 mg, TOKYO KASEI KOGYO) and sodium borohydride (1.2 g, nacalai tesque) were added and stirred at room temperature for 4 hours. Insoluble materials were filtered out and the filtrate was distilled under reduced pressure to remove the solvent. The residue was purified by silica gel chromatography (eluent; chloroform) and concentrated to yield the compound (XXVI) (3.4 g) as a pale yellow amorphous solid.

Rf=0.40 (ethyl acetate:n-hexane=1:1),

Mass: 486 (MH$^+$)

$^1$H-NMR (CDCl$_3$): 2.68 (1H, dd, J=12.8, 10.2), 2.84 (1H, dd, J=13.0, 3.4), 3.01 (1H, dt, J=5.0, 14.2), 3.14 (1H, dt, J=5.9, 14.2), 3.72 (1H, d, J=13.5), 3.96 (2H, m), 4.11 (2H, m), 4.61 (1H, dd, J=3.4, 10.0), 6.60 (1H, dd, J=2.0, 8.2), 6.76 (1H, d, J=2.0), 6.86 (2H, m), 7.14–7.37 (9H, m), 7.90–7.98 (3H, m)

HPLC: retention time (6.4 min) (column: WAKOSIL-II 3C18AR (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 25° C.)

EXAMPLE 24

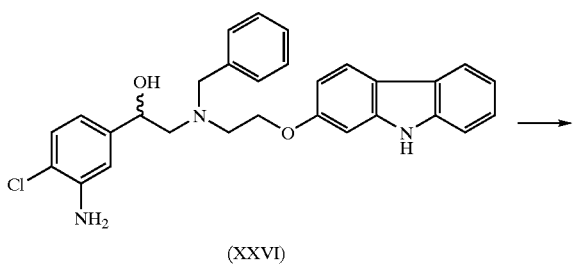

(XXVI)

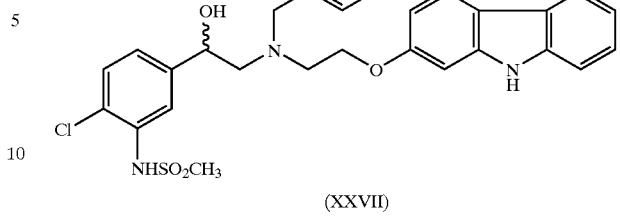

(XXVII)

The compound (XXVI) (240 mg) obtained in Example 23 was dissolved in tetrahydrofuran (5 ml), and pyridine (0.5 ml, Wako Pure Chemical Industries) was added and cooled to 0° C. Then, methanesulfonyl chloride (0.104 ml, Wako Pure Chemical Industries) was added and stirred at 0° C. for 4 hours. Chloroform (20 ml) and 1N hydrochloric acid (20 ml) were added to the reaction mixture and an organic layer was separated. The resulting organic layer was dried and distilled under reduced pressure to remove the solvent. The residue was purified by silica gel chromatography (eluent; chloroform) to yield the compound (XXVII) (105 mg) as a pale yellow amorphous solid.

$^1$H-NMR (CDCl$_3$): 2.70 (1H, dd, J=10.2, 13.2), 2.93 (1H, dd, J=3.6, 13.2), 2.98 (3H, s), 3.02–3.07 (1H, m), 3.10–3.16 (1H, m), 3.74 (1H, d, J=13.5), 3.99 (1H, d, J=13.5), 4.08–4.16 (2H, m), 4.28 (1H, br.), 4.77 (1H, dd, J=3.6, 10.2), 6.84 (1H, dd, J=2.2, 8.5), 6.98 (1H, d, J=2.2), 7.12–7.42 (10H, m), 7.65 (1H, d, J=2.2), 7.93 (1H, d, J=8.5), 7.97 (1H, d, J=7.7), 8.15 (1H, brs)

HPLC: retention time (6.2 min) (column: WAKOSIL-II 3C18AR (Wako Pure Chemical Industries; 4.6 mm ID×50 mm), solvent: 20 mM aqueous sodium dihydrogenphosphate solution (pH 2.9)/acetonitrile=(0 min) 70/30-(5 min) 10/90, then held at 10/90, flow rate: 1.0 ml/min, detection wave length: 233 nm, 25° C.)

EXAMPLE 25

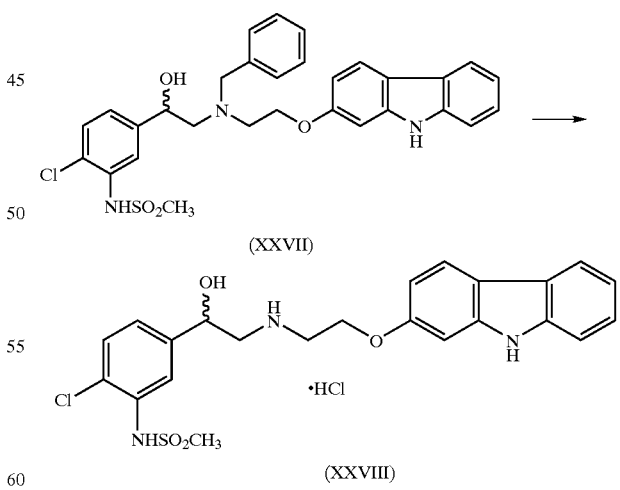

(XXVII)

(XXVIII)

The compound (XXVII) (55 mg) obtained in Example 24 was dissolved in a mixed solvent of tetrahydrofuran (2 ml) and methanol (2 ml), and 2N hydrochloric acid (0.1 ml) was added and cooled with ice. Then, 5% palladium-carbon (Palladium, sulfided, 5 wt. % (dry basis) on carbon) (10 mg, Aldrich) was added and stirred for 24 hours under a hydrogen atmosphere at atmospheric pressure while ice cooling. The reaction mixture was allowed to warm to room temperature and methanol (4 ml) was added to the precipitate. After filtering the catalyst, the catalyst was washed twice with methanol (2 ml) and distilled under reduced pressure to remove the solvent. The residue was dried under reduced pressure at 40° C. to yield the compound (XXVIII) (49 mg) as a white solid.

The thus obtained compound had the same retention time in HPLC as the compound obtained according to the known method of JP-A-9-249623, indicating that both compounds were identical with each other.

HPLC: retention time (16.8 min) (column; YMC-pack Pro C18 AS302 (YMC; 4.6 mm ID×150 mm), eluent: 20 mM aqueous sodium dihydrogenphosphate solution (pH 2.9)/acetonitrile=(0 min) 80/20-(20 min) 65/35, flow rate: 1.0 ml/min, detection wave length 233 nm, 40° C.)

EXAMPLES 26 to 31

In the synthesis of the compound (VII) from the compound (VI) as in Example 5, [(S,S)-N-methanesulfonyl-1,2-diphenylethylenediamine](p-cymene) ruthenium complex used in Example 5 was replaced by various catalysts as shown in Table 1. Specifically, the compound (VI) (200 mg) obtained in Example 1 was reacted as in Example 5 using the catalyst, formic acid/triethylamine complex and solvent as shown in Table 1.

Relative area percents of the compound (VI) and the compound (VII) were measured in the HPLC analysis of the reaction mixture at the time shown in Table 1. All the optical purities were 80% ee or higher.

HPLC: retention time (compound (VI): 8.4 min, compound (VII): 5.4 min) (column: COSMOSIL ODS-5 (GL Science; 4.6 mm ID×150 mm), solvent: 50 mM aqueous potassium dihydrogenphosphate solution/acetonitrile=6/4, flow rate: 1.0 ml/min, detection wave length: 254 nm, 25° C.)

EXAMPLE 32

To a solution of the compound (X) (10.0 g) obtained in Example 8 in tetrahydrofuran (50 ml), sodium hydrogencarbonate (9.30 g, Wako Pure Chemical Industries) was added and cooled to 0° C. Then, methanesulfonic acid anhydride (5.02 g, Aldrich) was added so that the internal temperature did not exceed 5° C., and stirred at 0° C. for 6 hours. Water (150 ml) and ethyl acetate (100 ml) were added to the reaction mixture and the separated organic layer was sequentially washed three times with aqueous saturated sodium bicarbonate (100 ml) and once with aqueous saturated sodium chloride (100 ml).

Then, without isolating the produced compound (XI), methanol (83 ml) was added to the organic layer and then 10% palladium-carbon (water content 50%) (0.94 g, N.E. CHEMCAT) was further added. Under a hydrogen atmosphere at atmospheric pressure, the organic layer was stirred at the internal temperature of about 40° C. for 4 hours. After cooling, tetrahydrofuran (40 ml) was added and stirred at

TABLE 1

| Ex. | Catalyst RuCl[(S,S)-R$^4$SO$_2$-DPEN] (p-cymene)* Substituent R$^4$ | mmol | Formic acid/NEt$_3$ = 5/2 [ml] | Solvent Kind | Solvent [ml] | Stir Temp [° C.] | Stir Time [hr] | Compound (VI) (%) | Compound (VII) (%) |
|---|---|---|---|---|---|---|---|---|---|
| 26 | —C$_6$H$_4$—CH$_3$ (para) | 0.01 | 0.5 | THF | 0.5 | 5 | 26 | 0 | 90.5 |
| 27 | —C$_6$H$_5$ | 0.01 | 0.5 | THF | 0.5 | 5 | 20 | 0 | 91.4 |
| 28 | —C$_6$H$_4$—CH$_3$ (ortho) | 0.01 | 0.5 | THF | 0.5 | 5 | 26 | 3.3 | 83.7 |
| 29 | —C$_6$H$_4$—OCH$_3$ (para) | 0.01 | 0.5 | THF | 0.5 | 5 | 26 | 1.8 | 85.5 |
| 30 | —C$_6$H$_4$—F (para) | 0.01 | 0.5 | THF | 0.5 | 5 | 26 | 0 | 87.7 |
| 31 | —CH$_3$ | 0.01 | 0.5 | THF | 0.5 | 5 | 20 | 0 | 93.1 |

*chloro-[(S,S)—N—R$^4$SO$_2$-1,2-diphenylethylenediamine] (p-cymene) ruthenium complex room temperature for 30 minutes followed by filtration. The residue was washed with tetrahydrofuran (8 ml) and the filtrate and the washing solution were combined. The solvent was distilled off under reduced pressure to yield the compound (XII) (9.0 g) as a pale yellow solid.

The thus obtained compound (XII) had the same properties in TLC and HPLC as the compound (XII) obtained in Example 10, indicating that the both compounds were identical with each other.

EXAMPLE 33

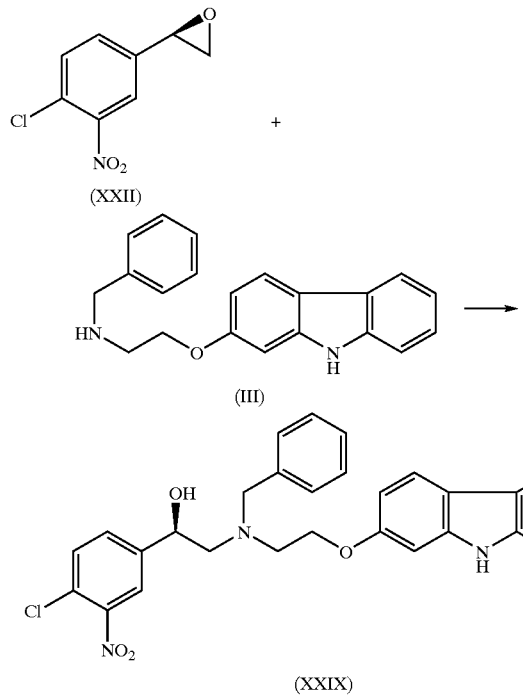

(XXII)

(III)

(XXIX)

The procedures of Example 22 were repeated using the compound (XXII) obtained in Example 19 instead of the compound (XXIV) of the Example 22, to yield the compound (XXIX).

HPLC: retention time (37.3 min) (column: CHIRALCEL AD (DAICEL CHEMICAL INDUSTRIES; 4.6 mm ID×250 mm), eluent: Hexane/EtOH=20/80, flow rate: 0.5 ml/min, detection wave length: 233 nm, room temperature. The retention time of S-form was 43.3 minutes.

EXAMPLE 34

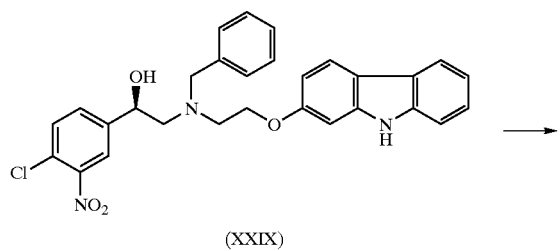

(XXIX)

-continued

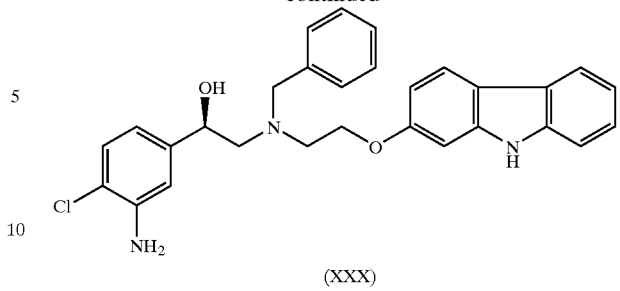

(XXX)

The procedures of Example 23 were repeated using the compound (XXIX) obtained in Example 33 instead of the compound (XXV) of Example 23, to yield the compound (XXX).

HPLC: retention time (42.4 min) (column: CHIRALCEL AD (DAICEL CHEMICAL INDUSTRIES; 4.6 mm ID×250 mm), eluent: Hexane/EtOH=20/80, flow rate: 0.5 ml/min, detection wave length: 233 nm, room temperature. The retention time of S-form was 36.9 minutes.

EXAMPLE 35

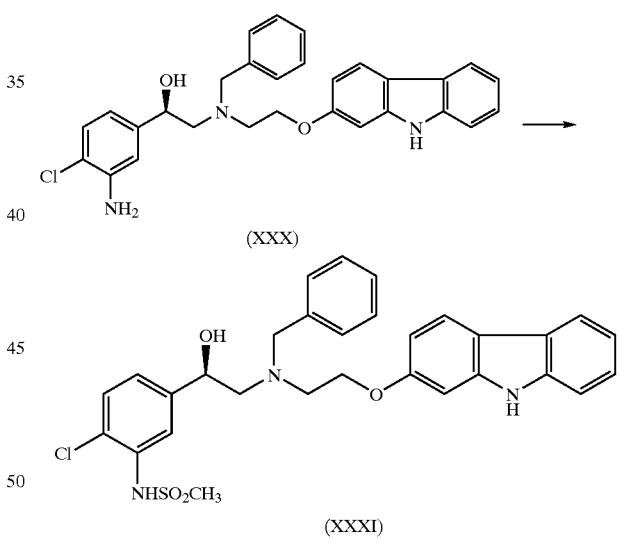

(XXX)

(XXXI)

The procedures of Example 24 were repeated using the compound (XXX) obtained in Example 34 instead of the compound (XXVI) of Example 24, to yield as the compound (XXXI).

HPLC: retention time (22.1 min) (column: CHIRALCEL AD (DAICEL CHEMICAL INDUSTRIES; 4.6 mm ID×250 mm), eluent: Hexane/EtOH=20/80, flow rate: 0.5 ml/min, detection wave length: 233 nm, room temperature. The retention time of S-form was 27.4 minutes.

EXAMPLE 36

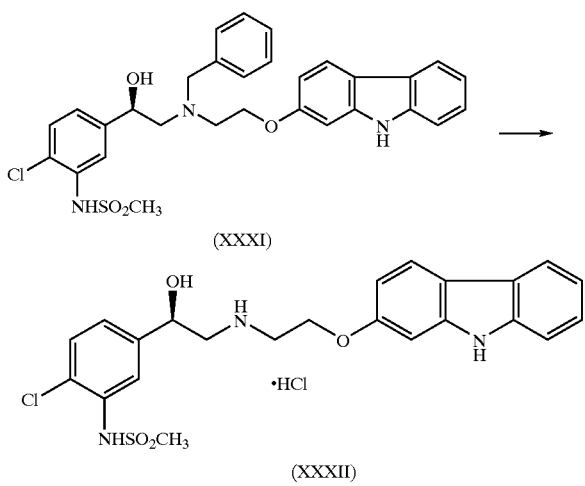

The procedures of Example 25 were repeated using the compound (XXXI) obtained in Example 35 instead of the compound (XXVII) of Example 25, to yield the compound (XXXII).

The thus obtained compound had the same retention time in HPLC as the compound obtained according to the known method (JP-A-9-249623), thus confirming that the both compounds were identical with each other.

EXAMPLE 37

Synthesis of (R)-2-[N-[2-(6-hydroxy-9H-carbazol-2-yloxy)]ethyl]amino-1-(3-methylsulfonylamino) phenylethanol hydrochloride Step A: Synthesis of 2-methoxy-6-hydroxycarbazole 2-Nitro-4-methoxyaniline (16.8 g) was added to water (30 ml) and concentrated hydrochloric acid (160 ml), and stirred at room temperature for 20 minutes and then at 70° C. for 75 minutes. The reaction mixture was cooled with ice and an aqueous solution (30 ml) of sodium nitrite (11.5 g) was dropwise added so that the temperature of the reaction solution did not exceed 5° C. After addition, the mixture was stirred for 1 hour while the temperature was maintained at 10° C. The reaction mixture was filtered and the residue was washed with water (50 ml). The filtrate was cooled with ice, to which an aqueous solution (120 ml) of sodium hydrogencarbonate (123 g) and 1,4-benzoquinone (12.3 g) was dropwise added over 1 hour. After addition, the reaction mixture was stirred for 4 hours while ice cooling and then filtered. The crystal was washed with water and dried. The resulting crystal was dissolved in methanol (200 ml) and acetic acid (20 ml), and 10% palladium/carbon (1.0 g) was added thereto and stirred under a hydrogen atmosphere at room temperature for 3 hours. The reaction mixture was filtered and the residue was washed with methanol (30 ml). Under ice cooling, concentrated aqueous ammonia (50 ml) was dropwise added to the filtrate over 5 minutes. After addition, the mixture was allowed to warm to room temperature and stirred for 12 hours. The reaction mixture was filtered and the crystal was washed with water and dried in vacuo. The resulting crude product was purified by silica gel column chromatography (hexane/ethyl acetate=3/1 to 0/1) to yield the titled compound (2.71 g).

Rf=0.38 (ethyl acetate:n-hexane=1:1)

$^1$H-NMR (DMSO-$d_6$): 3.82 (3H, s), 6.68 (1H, dd, J=2.2, 8.5), 6.77 (1H, dd, J=2.2, 8.5), 6.88 (1H, d, J=2.2), 7.20 (1H, d, J=8.5), 7.30 (1H, d, J=2.2), 7.83 (1H, d, J=8.5), 8.82 (1H, br), 10.73 (1H, br)

Step B: Synthesis of 2-methoxy-6-benzyloxycarbazole

The compound (3.90 g) synthesized in step A was dissolved in acetone (90 ml) and DMF (6 ml), to which potassium carbonate (10.1 g) and benzyl bromide (3.12 g) were added. The mixture was stirred at room temperature for 25 hours. Further, benzyl bromide (1.56 g) was added and stirred at room temperature for 24 hours. Water (500 ml) was added to the reaction mixture and the precipitated crystal was filtered out. The crystal was washed with water and dried in vacuo. The resulting crude product was added to ethyl acetate (40 ml) and stirred for 10 minutes followed by filtration of crystal. The crystal was dried in vacuo to yield the titled compound (3.28 g).

Rf=0.66 (ethyl acetate:n-hexane=1:1), $^1$H-NMR (DMSO-$d_6$): 3.83 (3H, s), 5.16 (2H, s), 6.73 (1H, dd, J=2.2, 8.5), 6.92 (1H, d, J=2.2), 6.99 (1H, dd, J=2.5, 8.5), 7.30–7.43 (4H, m), 7.50–7.52 (2H, m), 7.67 (1H, d, J=2.2), 7.92 (1H, d, J=8.5), 10.90 (1H, br).

Step C: Synthesis of 2-hydroxy-6-benzyloxycarbazole

The compound (5.93 g) obtained in step B was dissolved in DMSO (110 ml), and sodium cyanide (5.75 g) was added to the mixture and stirred at 170° C. for 7 hours. Water (150 ml) was added to the reaction mixture and extracted with ethyl acetate. The organic layer was washed with water and dried, and the solvent was distilled off under reduced pressure. The residue was purified by silica gel column chromatography (hexane/ethyl acetate=1/1) to yield the titled compound (1.24 g) as a 1:1 mixture with 2-methoxy-6-hydroxycarbazole.

Rf=0.69 (ethyl acetate:n-hexane=1:1).

The following is a spectrum of 2-hydroxy-6-benzyloxycarbazole.

$^1$H-NMR (DMSO-$d_6$): 5.15 (2H, s), 6.59 (1H, dd, J=2.2, 8.2), 6.76 (1H, d, J=2.5), 6.95 (1H, dd, J=2.5, 8.5), 7.26 (1H, d, J=8.5), 7.32–7.43 (3H, m), 7.49–7.52 (2H, m), 7.60 (1H, d, J=2.5), 7.80 (1H, d, J=8.2), 9.35 (1H, br), 10.72 (1H, br)

Step D: Synthesis of (R)-2-[N-[2-(6-hydroxy-9H-carbazol-2-yloxy)]ethyl]amino-1-(3-methylsulfonylamino) phenylethanol hydrochloride 2-(N-benzylaminoethoxy)-6-benzyloxy-9H-carbazole was synthesized from the compound obtained in step C according to the preparation of Reference Example.

The procedures of Example 7 were repeated except that the compound (III) was replaced by 2-(N-benzylaminoethoxy)-6-benzyloxy-9H-carbazole, and the product was purified by silica gel column to yield a 6-benzyloxy derivative of the compound (IX). Further, according to Examples 8 to 10, a free form of the titled compound was obtained. 0.5N alcoholic hydrochloric acid (3.9 ml) was added to the titled compound in the free form and concentrated. The precipitated crystal was filtered, washed with cold methanol and dried to yield the titled compound.

$^1$H-NMR (DMSO-$d_6$): 3.00 (3H, s), 3.05–3.53 (4H, m), 4.33–4.42 (2H, m), 5.02 (1H, d, J=9.9), 6.27 (1H, br), 6.75 (1H, dd, J=2.2, 8.5), 6.80 (1H, dd, J=2.2, 8.5), 6.95 (1H, d, J=2.2), 7.13–7.24 (3H, m), 7.31–7.39 (3H, m), 7.88 (1H, d, J=8.5), 8.88 (1H, br), 8.99 (1H, br), 9.24 (1H, br), 9.86 (1H, br), 10.85 (1H, br)

EXAMPLE 38

3'-Nitroacetophenone (2.00 g) was suspended in methyl t-butyl ether (12.1 ml), and sulfuryl chloride (4.90 g) was dropwise added thereto at 20° C. over 15 minutes. After stirring for 2 hours, precipitated solids were filtered and washed with methyl t-butyl ether. Drying under reduced pressure yielded the desired 2-chloro-3'-nitroacetophenone (1.62 g; 67.0%).

EXAMPLE 39

3'-Nitroacetophenone (2.00 g) was dissolved in tetrahydrofuran (24.2 ml), and sulfuryl chloride (4.90 g) was dropwise added thereto at 22° C. over 15 minutes. After stirring for 2 hours, water (150 ml) was added to the reaction mixture and stirred for 1 hour. Ethyl acetate was added, and the separated organic layer was washed with aqueous saturated sodium bicarbonate/aqueous saturated sodium chloride mixed solvent. After drying over anhydrous sodium sulfate, the solvent was distilled off under reduced pressure. Diethyl ether was added to the residue and stirred, and the precipitated crystal was then filtered and dried under reduced pressure to yield the desired 2-chloro-3'-nitroacetophenone (1.41 g; 58.3%).

EXAMPLE 40

3'-Nitroacetophenone (2.00 g) was dissolved in diisopropyl ether (12.1 ml) and sulfuryl chloride (6.70 g) was added all at once thereto at 22° C. and refluxed for 6.5 hours. The reaction mixture was allowed to cool to room temperature while stirring, and the precipitated solids were filtered and washed with diisopropyl ether. Drying under reduced pressure yielded the desired 2-chloro-3'-nitroacetophenone (2.01 g; 83.1%).

EXAMPLE 41

4'-Chloro-3'-nitroacetophenone (2.00 g) was dissolved in tetrahydrofuran (20 ml), and sulfuryl chloride (4.04 g) was dropwise added over 75 minutes while maintaining at room temperature. After addition, stirring was further continued for 105 minutes. After the reaction, water (50 ml) was added and extracted with ethyl acetate. The organic layer was washed with aqueous saturated sodium chloride and dried over anhydrous sodium sulfate, and the solvent was distilled off under reduced pressure. The residue was purified by silica gel column chromatography to yield the desired 2-chloro-(4'-chloro-3'-nitro)acetophenone (1.60 g; 68.2%).

EXAMPLES 42 to 47

(18)

| acetophenone derivative | $R^{13}$ | $R^{14}$ |
|---|---|---|
| 1 | $NO_2$ | H |
| 2 | $NO_2$ | Cl |
| 3 | H | Br |
| 4 | H | H |

An acetophenone (2.00 g) as shown by the formula (18) was dissolved or suspended in a solvent as shown in Table 2 (M representing the molarity based on the acetophenone derivative), and sulfuryl chloride in an amount as shown in Table 2 was added all at once under stirring. The temperature and reaction time were as shown in Table 2.

TABLE 2

| Ex. | Solvent(M) | Acetophenone derivative | $SO_2Cl_2$ (equivalent) | Temp. | Time (hr) | Yield (%) |
|---|---|---|---|---|---|---|
| 42 | MTBE(0.5) | 1 | 3.0 | r.t. | 4.5 | 50.8 |
| 43 | MTBE(1) | 1 | 1.65 | reflux | 7.0 | 70.1 |
| 44 | IPE(1) | 1 | 3.0 | r.t. | 3.0 | 77.8 |
| 45 | DME(1) | 1 | 1.65 | r.t. | 4.0 | 71.4 |
| 46 | MTBE(1) | 3 | 3.0 | r.t. | 1.0 | 50.3 |
| 47 | MTBE(1) | 4 | 1.1 | r.t. | 7.0 | 78.9 |

MTBE: methyl t-butyl ether; IPE: diisopropyl ether; DME: 1,2-dimethoxyethane

Comparative Examples 1 to 3

For comparison, other solvents as shown in Table 3 were used. Methods were as shown in Examples.

TABLE 3

| Comparative Ex. | Solvent (M) | Acetophenone derivative | $SO_2Cl_2$ (equivalent) | Temp. | Time (hr) | Yield (%) |
|---|---|---|---|---|---|---|
| 1 | $CH_2Cl_2$ (1) | 1 | 3.0 | r.t. | 7.0 | ≦10 |
| 2 | Toluene (1) | 1 | 3.3 | reflux | 7.0 | ≦10 |
| 3 | $CH_3OH$ (1) | 1 | 3.0 | r.t. | 7.0 | ≦10 |

All publications, patents and patent applications cited herein are incorporated herein by reference.

INDUSTRIAL APPLICABILITY

According to the present invention, a novel process for the preparation of tricyclic amino alcohol derivatives and their salts useful in the treatment and prevention of diabetes, obesity, hyperlipidemia and the like, and intermediates useful in the process are provided.

What is claimed is:

1. A process for the preparation of a compound of the formula (1):

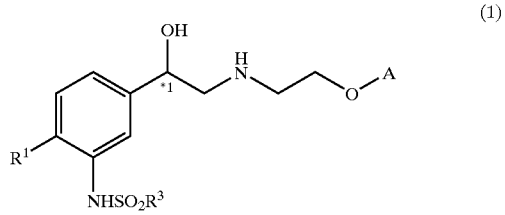

(1)

wherein $R^1$ represents a hydrogen or halogen atom, or a hydroxyl group, $R^3$ represents a lower alkyl group or a benzyl group, *1 represents an asymmetric carbon atom, and A represents one of the following groups:

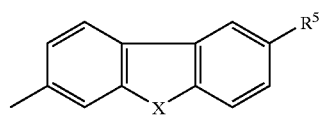

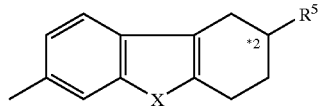

wherein X represents NH, O or S, $R^5$ represents a hydrogen atom, or a hydroxyl, amino or acetylamino group, *2 represents an asymmetric carbon atom when $R^5$ is not a hydrogen atom, said process comprising:

reducing a compound of the formula (7):

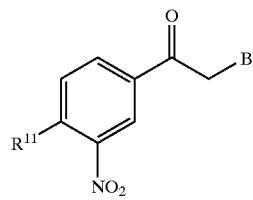

(7)

wherein $R^{11}$ represents a hydrogen or halogen atom, or a protected hydroxyl group, B represents a chlorine or bromine atom, to give a halohydrin of the formula (6):

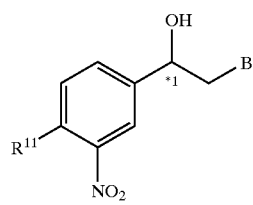

(6)

wherein $R^{11}$, B and *1 are as defined above; and, converting the halohydrin under alkaline conditions into an epoxy compound of the formula (5):

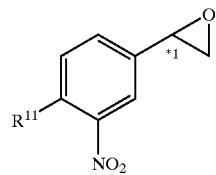

(5)

wherein $R^{11}$ and *1 are as defined above; and, reacting the epoxy compound with a compound of the formula (9):

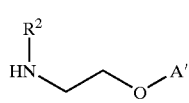

(9)

wherein $R^2$ represents an amino-protecting group, and A' represents one of the following groups:

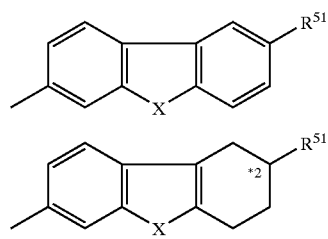

wherein X represents NH, O or S, $R^{51}$ represents a hydrogen atom a protected hydroxyl group, a protected amino group or an acetylamino group, and *2 represents an asymmetric carbon atom when $R^{51}$ is not a hydrogen atom, to give an amino alcohol of the formula (4):

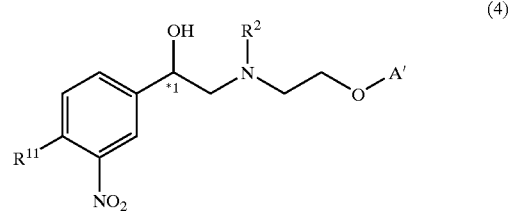

(4)

wherein $R^{11}$, $R^2$, A' and *1 are as defined above; and, reducing the nitro group to give an aniline derivative of the formula (3):

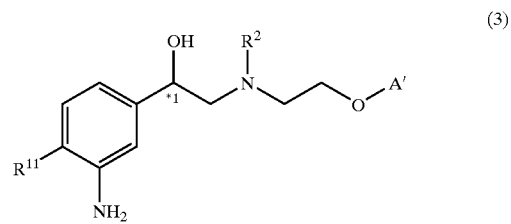

(3)

wherein $R^{11}$, $R^2$, A' and *1 are as defined above; and, reacting the aniline derivative with a sulfonating agent to give an amino alcohol of the formula (2):

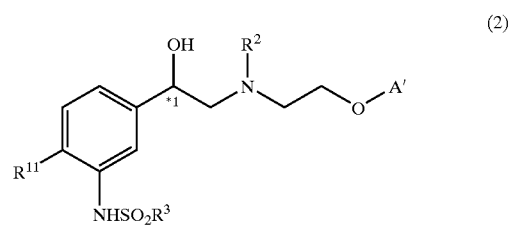

(2)

wherein $R^3$, $R^{11}$, $R^2$, A' and *1 are as defined above; and then, simultaneously or sequentially removing the protecting groups to give the compound of the formula (1).

2. A process for the preparation of a compound of the formula (1):

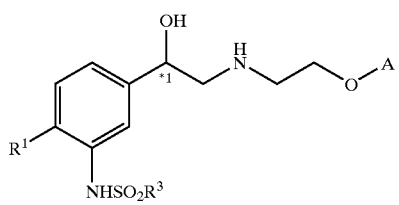
(1)

wherein $R^1$ represents a hydrogen or halogen atom, $R^3$ represents a lower alkyl group or a benzyl group, *1 represents an asymmetric carbon atom, and A represents one of the following groups:

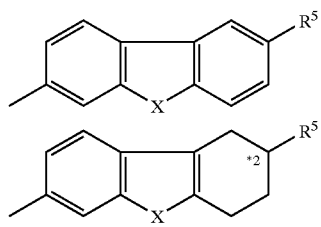

wherein X represents NH, O or S, $R^5$ represents a hydrogen atom, or a hydroxyl, amino or acetylamino group, and *2 represents an asymmetric carbon atom when $R^5$ is not a hydrogen atom,
said process comprising:
  chlorinating a compound of the formula (18):

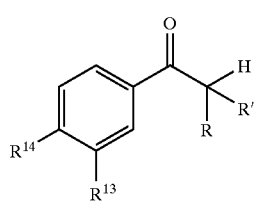
(18)

wherein $R^{14}$ represents a hydrogen or halogen atom, $R^{13}$ represents nitro, and both R and R' represent a hydrogen atom, with sulfuryl chloride in an ether solvent, to give a compound of the formula (19):

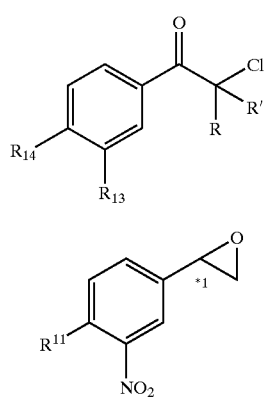

wherein $R^{11}$ and *1 are as defined above; and,
reacting the epoxy compound with a compound of the formula (9):

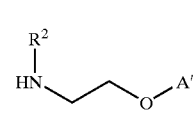
(9)

wherein $R^2$ represents an amino-protecting group, and A' represents one of the following groups:

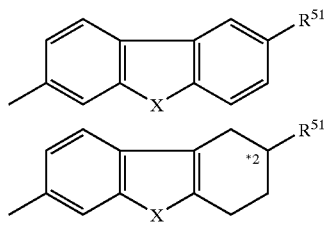

wherein X represents NH, O or S, $R^{51}$ represents a hydrogen atom, a protected hydroxyl group, a protected amino group or an acetylamino group, and *2 represents an asymmetric carbon atom when $R^{51}$ is not a hydrogen atom, to give an amino alcohol of the formula (4):

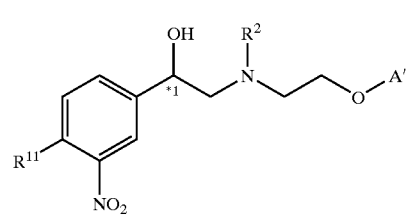
(4)

wherein $R^{11}$, $R^2$, A' and *1 are as defined above; and, reducing the nitro group to give an aniline derivative of the formula (3):

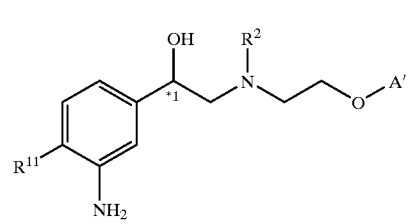
(3)

wherein $R^{11}$, $R^2$, A' and *1 are as defined above; and, reacting the aniline derivative with a sulfonating agent to give an amino alcohol of the formula (2):

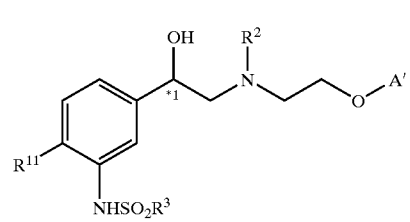
(2)

wherein $R^3$, $R^{11}$, $R^2$, A' and *1 are as defined above; and then,
simultaneously or sequentially removing the protecting groups to give the compound of the formula (1).

3. A process for the preparation a compound of the formula (1):

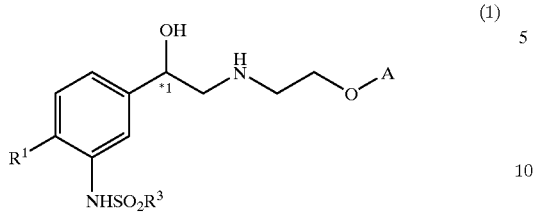
(1)

wherein $R^1$ represents a hydrogen or halogen atom, or a hydroxyl group, $R^3$ represents a lower alkyl group or a benzyl group, *1 represents an asymmetric carbon atom, and A represents one of the following groups:

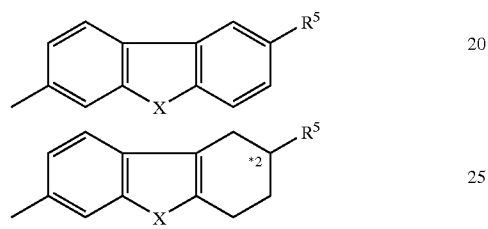

wherein X represents NH, O or S, $R^5$ represents a hydrogen atom, or a hydroxyl, amino or acetylamino group, *2 represents an asymmetric carbon atom when $R^5$ is not a hydrogen atom, said process comprising:

reacting an epoxy compound of the formula (5):

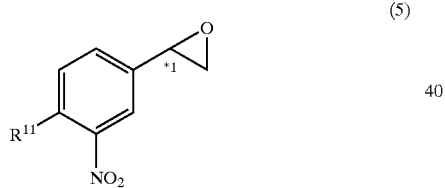
(5)

wherein $R^{11}$ represents a hydrogen or halogen atom, or a protected hydroxyl group, and *1 has the same meaning as defined above, with a compound of the formula (9):

(9)

wherein $R^2$ represents a protective group for the amino group, and A' represents one of the following groups:

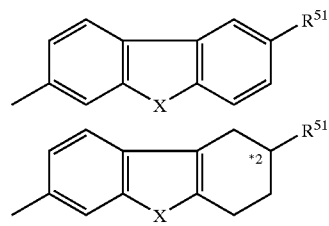

wherein X represents NH, O or S, $R^{51}$ represents a hydrogen atom, a hydroxyl group protected by a protective group, an amino group protected by a protective group or an acetylamino group, and *2 represents an asymmetric carbon atom when $R^{51}$ is not a hydrogen atom, to give an amino alcohol of the formula (4):

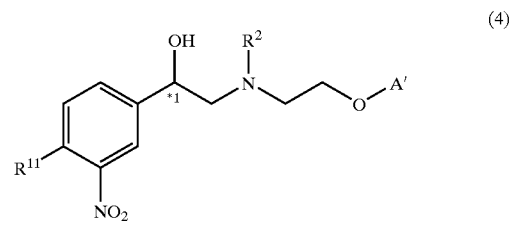
(4)

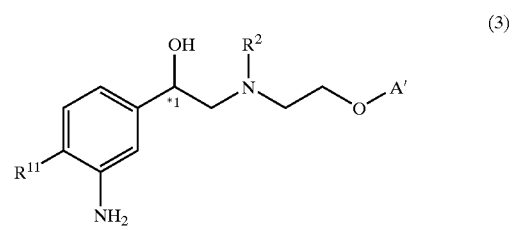
(3)

wherein $R^{11}$, $R^2$, A' and *1 are as defined above; and, reacting the aniline derivative with a sulfonating agent to give an amino alcohol of the formula (2):

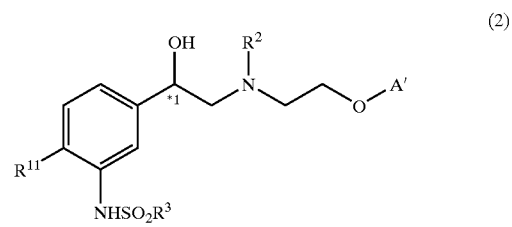
(2)

wherein $R^3$, $R^{11}$, $R^2$, A' and *1 are as defined above; and then, simultaneously or sequentially removing the protective groups to give the compound of the formula (1).

* * * * *